US012580910B2

(12) United States Patent
Soon-Shiong et al.

(10) Patent No.: US 12,580,910 B2
(45) Date of Patent: Mar. 17, 2026

(54) SYNTHETIC GENOMIC VARIANT-BASED SECURE TRANSACTION DEVICES, SYSTEMS AND METHODS

(71) Applicants:NantHealth, Inc., Culver City, CA (US); NantOmics, LLC, Culver City, CA (US); Nant Holdings IP, LLC, Culver City, CA (US)

(72) Inventors: Patrick Soon-Shiong, Los Angeles, CA (US); Stephen Benz, Santa Cruz, CA (US); Rahul Chaturvedi, San Diego, CA (US)

(73) Assignee: NantOmics, LLC, Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 18/747,350

(22) Filed: Jun. 18, 2024

(65) Prior Publication Data

US 2025/0023868 A1     Jan. 16, 2025

Related U.S. Application Data

(63) Continuation of application No. 18/084,449, filed on Dec. 19, 2022, now Pat. No. 12,052,240, which is a (Continued)

(51) Int. Cl.
    *H04L 9/40*        (2022.01)
    *G06F 21/32*       (2013.01)
    (Continued)

(52) U.S. Cl.
    CPC .......... *H04L 63/0861* (2013.01); *G06F 21/32* (2013.01); *G06F 21/35* (2013.01);
    (Continued)

(58) Field of Classification Search
    CPC ......................... G06Q 30/018; H04L 63/0861
    See application file for complete search history.

(56) References Cited

U.S. PATENT DOCUMENTS 6,711,293  B1     3/2004  Lowe
7,529,718  B2     5/2009  Lambert
                  (Continued)

FOREIGN PATENT DOCUMENTS

JP        2002-288605 A    10/2002
JP        2004-208994 A     7/2004
                  (Continued)

OTHER PUBLICATIONS

First Examination Report issued in Australian Patent Application No. 2015311866 dated Oct. 25, 2017, 4 pages.

(Continued)

*Primary Examiner* — Ojo O Oyebisi
(74) *Attorney, Agent, or Firm* — MASCHOFF BRENNAN; Andrew Noble; Elaine K. Lee

(57)            ABSTRACT

Various devices, systems, structures and methods are disclosed related to securely authorizing a transaction by synchronizing digital genomic data with associated synthetic genomic variants. An embodiment of the present invention utilizes digital genomic data associated with an entity, such as a person, who may utilize a genome-based security device to complete a transaction. In one embodiment, a person may use a genome-based security device to communicate with an external device over a wireless or other communication interface, synchronize digital genomic data and an associated synthetic variant received from the external device with digital genomic data and associated synthetic variant stored on the genome-based security device.

20 Claims, 7 Drawing Sheets

Specification includes a Sequence Listing.

Related U.S. Application Data continuation of application No. 17/707,925, filed on Mar. 29, 2022, now Pat. No. 11,785,004, which is a continuation of application No. 16/034,271, filed on Jul. 12, 2018, now Pat. No. 11,785,002, which is a continuation of application No. 14/844,974, filed on Sep. 3, 2015, now Pat. No. 10,050,959.

(60) Provisional application No. 62/137,129, filed on Mar. 23, 2015, provisional application No. 62/077,683, filed on Nov. 10, 2014, provisional application No. 62/062,023, filed on Oct. 9, 2014, provisional application No. 62/057,922, filed on Sep. 30, 2014, provisional application No. 62/045,062, filed on Sep. 3, 2014.

(51) Int. Cl.

| | | |
|---|---|---|
| *G06F 21/35* | (2013.01) | |
| *G16B 50/00* | (2019.01) | |
| *G16B 50/30* | (2019.01) | |
| *H04L 9/08* | (2006.01) | |
| *H04L 9/32* | (2006.01) | |

(52) U.S. Cl.
CPC ............ *G16B 50/00* (2019.02); *G16B 50/30* (2019.02); *H04L 9/0872* (2013.01); *H04L 9/3231* (2013.01); *H04L 63/0853* (2013.01); *H04L 2463/102* (2013.01)

(56) References Cited

U.S. PATENT DOCUMENTS

| | | | |
|---|---|---|---|
| 8,554,136 | B2 | 10/2013 | Mccormack |
| 8,689,008 | B2 | 4/2014 | Rangadass et al. |
| 8,714,459 | B2 | 5/2014 | Mccormack et al. |
| 8,757,501 | B2 | 6/2014 | Mccormack et al. |
| 8,811,526 | B2 | 8/2014 | Mccormack et al. |
| 8,825,555 | B2 | 9/2014 | Gross et al. |
| 9,269,418 | B2 | 2/2016 | Felton et al. |
| 9,386,481 | B2 | 7/2016 | Li et al. |
| 9,461,914 | B2 | 10/2016 | Kandasamy et al. |
| 10,050,959 | B2 | 8/2018 | Soon-Shiong et al. |
| 11,785,002 | B2 | 10/2023 | Soon-Shiong et al. |
| 11,785,004 | B2 | 10/2023 | Soon-Shiong et al. |
| 12,052,240 | B2 | 7/2024 | Soon-Shiong et al. |
| 2002/0129251 | A1 | 9/2002 | Itakura et al. |
| 2003/0046237 | A1 | 3/2003 | Uberti |
| 2004/0236701 | A1 | 11/2004 | Beenau et al. |
| 2005/0026117 | A1 | 2/2005 | Judson et al. |
| 2005/0060556 | A1 | 3/2005 | Jonas |
| 2005/0158767 | A1 | 7/2005 | Haskell et al. |
| 2007/0050314 | A1 | 3/2007 | Martin et al. |
| 2009/0110192 | A1 | 4/2009 | Elrod et al. |
| 2009/0183008 | A1 | 7/2009 | Jobmann |
| 2010/0070292 | A1 | 3/2010 | Kenedy et al. |
| 2010/0121872 | A1 | 5/2010 | Subramaniam |
| 2010/0273147 | A1 | 10/2010 | Valenti et al. |
| 2010/0280763 | A1 | 11/2010 | Fernandez |
| 2011/0313787 | A1 | 12/2011 | Rangadass et al. |
| 2012/0059670 | A1 | 3/2012 | Sanborn et al. |
| 2012/0066001 | A1 | 3/2012 | Sanborn et al. |
| 2012/0300645 | A1 | 11/2012 | Li et al. |
| 2013/0054272 | A1 | 2/2013 | Rangadass et al. |
| 2013/0144653 | A1 | 6/2013 | Poe et al. |
| 2013/0166317 | A1 | 6/2013 | Beardall et al. |
| 2013/0205080 | A1 | 8/2013 | Felton et al. |
| 2013/0304496 | A1 | 11/2013 | Rangadass |
| 2013/0304512 | A1 | 11/2013 | Seshadri et al. |
| 2013/0307670 | A1 | 11/2013 | Ramaci |
| 2014/0012843 | A1 | 1/2014 | Soon-Shiong |
| 2014/0045706 | A1 | 2/2014 | Fan et al. |
| 2014/0074696 | A1 | 3/2014 | Glaser |
| 2014/0081665 | A1 | 3/2014 | Holmes |

| | | | |
|---|---|---|---|
| 2014/0108823 | A1 | 4/2014 | Rudelic et al. |
| 2014/0121116 | A1 | 5/2014 | Richards et al. |
| 2014/0180859 | A1 | 6/2014 | Cline et al. |
| 2014/0214903 | A1 | 7/2014 | Stivoric et al. |
| 2014/0226954 | A1 | 8/2014 | Miyasaka |
| 2014/0273856 | A1 | 9/2014 | Kyles et al. |
| 2014/0279203 | A1 | 9/2014 | Malek et al. |
| 2014/0289536 | A1 | 9/2014 | Maccarthy et al. |
| 2015/0026785 | A1 | 1/2015 | Soon-Shiong |
| 2015/0254912 | A1* | 9/2015 | Weisman .............. H04L 9/0866 |
| | | | 705/325 |
| 2015/0288603 | A1 | 10/2015 | Kandasamy et al. |
| 2016/0248769 | A1 | 8/2016 | Han et al. |
| 2019/0020651 | A1 | 1/2019 | Soon-Shiong et al. |
| 2022/0224686 | A1 | 7/2022 | Soon-Shiong et al. |
| 2023/0262055 | A1 | 8/2023 | Soon-Shiong et al. |

FOREIGN PATENT DOCUMENTS

| | | |
|---|---|---|
| JP | 2010-020524 A | 1/2010 |
| JP | 2011-003085 A | 1/2011 |
| JP | 2014-154085 A | 8/2014 |
| JP | 5631312 B2 | 11/2014 |
| WO | 2004/088585 A2 | 10/2004 |
| WO | 2013/030827 A1 | 3/2013 |
| WO | 2013/049420 A1 | 4/2013 |
| WO | 2013/126221 A1 | 8/2013 |
| WO | 2014/008434 A2 | 1/2014 |
| WO | 2014/040964 A1 | 3/2014 |
| WO | 2014/144548 A2 | 9/2014 |
| WO | 2014/170006 A1 | 10/2014 |

OTHER PUBLICATIONS

Gahi et al., "A Secure Database System using Homomorphic Encryption Schemes," DBKDA 2011 : The Third International Conference on Advances in Databases, Knowledge, and Data Applications, 2011, pp. 54-58.

International Preliminary Report on Patentability received for PCT Patent Application No. PCT/US2015/048386, mailed on Sep. 1, 2016, 5 pages.

International Search Report and Written Opinion received for PCT Patent Application No. PCT/US2015/048386, mailed on Dec. 17, 2015, 11 pages.

Metz, "A Credit Card Terminal That Takes Apps," MIT Technology Review, Oct. 29, 2014, 3 pages.

National Institute of Standards and Technology, "Security Requirements for Cryptographic Modules," FIPS Pub. 140-2, Jan. 11, 1994, U.S. Dept. of Commerce, U.S.

Office Action issued in Israeli Application No. 250716 dated Jan. 28, 2020, 18 pages.

Office Action received for Australian Patent Application No. 2018226429, mailed on Jul. 1, 2019, 3 pages.

Office Action received for Canadian Patent Application No. 2958478, mailed on Oct. 16, 2017, 4 pages.

Office Action received for Chinese Patent Application No. 201580047775.7, mailed on Dec. 16, 2019, 34 pages (23 pages of English Translation and 11 pages of Original Document).

Office Action received for Chinese Patent Application No. 201580047775.7, mailed on Jul. 2, 2020, 10 pages (6 pages of English Translation and 3 pages of Original Document).

Office Action received for Chinese Patent Application No. 201580047775.7, mailed on Mar. 4, 2019, 8 pages (5 pages of English Translation and 3 pages of Original Document).

Office Action received for European U.S. Appl. No. 15/838,857, mailed on Jan. 22, 2020, 4 pages.

Office Action received for Japanese Patent Application No. 2017-512396 , mailed on Jul. 9, 2019, 12 pages (5 pages of English Translation and 7 pages of Original Document).

Office Action received for Japanese Patent Application No. 2017-512396 , mailed on Jun. 26, 2018, 16 pages (8 pages of English Translation and 8 pages of Original Document).

Office Action received for Japanese Patent Application No. 2017-512396 , mailed on Nov. 6, 2018, 9 pages (4 pages of English Translation and 5 pages of Original Document).

(56)  References Cited

OTHER PUBLICATIONS

Office Action received for Korean Patent Application No. 10-2017-7008865, mailed on Nov. 7, 2018, 10 pages (5 pages of English Translation and 5 pages of Original Document).

Office Action received for Korean Patent Application No. 10-2019-7016056 , mailed on Aug. 9, 2019, 6 pages (3 pages of English Translation and 3 pages of Original Document).

Supplementary European Search Report and Search Opinion received for European Application No. 15838857.9, mailed on Mar. 21, 2018, 7 pages.

Trayanova, "Custom Cardiology: A Virtual Heart for Every Patient," IEEE Spectrum, Oct. 28, 2014, 8 pages.

* cited by examiner

Digital Genomic
Data
235

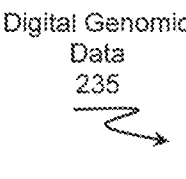

{SEQ ID NO: 3]
. ...GACTACACCATGAGGCCTTATTACAGTGTTAGTTTGTTCTGACAAATGCC
ATGCGTATTTTTAAGAACCTAAACATGCTTCTGAAGCTTAATAGACAAAAGC
CTCTTAAGGAAAAAAGAAAAGCACTGTTGAAGTCATGTACTTCTGTTAAAA
TCATAGCCTCTCTTTTAGACATATTTATGCTTCTGCTTACATTTTTAGATTT
TATTACTTGTTAGTAATTTGGATAGAATCATTCAGAGTTGTAAATTCAGGTA
GTAATAGAACTACTCAATTTTTCCAACTGTCTGTTTAGAAAGCTTTTTTT
TTGCATTCTTTATGTTTATTTATTTAAAATGCAACTATTTCTATGTAAATTT
AATATTAGATATTTATACATAAAAGACAACATGGTAGTATAATGACATCATA
TTCTTTTACTGTTTCATTGAAAATTACAAAGATAATATCTTTAGTTGATTT
TGTCACAGATACATATTATTTTTAATATACCAAGAACAGTATTTATATATTA
ATAAAAATCCTTTGGAAGTCT

Difference(s)
231
[SEQ ID NO:
2]

Block
238

---

Partition(s)
237

- Partition ID: 253D0897-9295-4052-A3CE-1D7F6190E152
- Location: Chromosome 14; 70,907,405
- Start: 70,907,405
- End: 71,115,385
- Length: 207,978
- Sequence:
    - Common: ...GACTACACCATGA...
    - Difference: TAATTTGGAT...TACAT
- Difference Measure: 0.03
- Strength: High
- Etc.

Partition
Database
250

| Account(s) 253 | Partition Identifier(s) 255 (GUIDs, UUIDs, Indices, Etc.) |
|---|---|
| Bank Account | DD1A59B9-21B3-47D6-AB26-1BB077ED5F35 |
| Credit Card Account | 84536195-6944-4E43-8CA2-464CDB328B65 |
| Insurance Account(s) | FA576EF0-CE48-40F3-AD63-AE00919CEF7F (Strength = low); 3AEAF1B0-8F41-4786-9CC7-0064F1A5AB6E (Strength = high) |
| Medical Records Key | B319D5CD-1A46-4043-8C29-9402B9AF1A06 |
| World of Warcraft® Password | 093499E3-B3BF-4191-98A0-5DE54A1659AB |
| Facebook® Password | ABBC065A-3668-42E1-9FBB-8BE0FDB7C87B |
| Etc. | ... |

Figure 2

SEQUENCE LISTING

```
Sequence total quantity: 5
SEQ ID NO: 1              moltype = DNA   length = 18
FEATURE                   Location/Qualifiers
source                    1..18
                          mol_type = genomic DNA
                          organism = Homo sapiens
SEQUENCE: 1
agtcgattac ataggact                                              18

SEQ ID NO: 2              moltype = DNA   length = 163
FEATURE                   Location/Qualifiers
source                    1..163
                          mol_type = genomic DNA
                          organism = Homo sapiens
SEQUENCE: 2
taatttggat agaatcattc agagttgtaa attcaggtag taatagaact actcaatttt   60
tccaactgtc tgtttagaaa agcttttttt tttgcattct ttatgtttat ttatttaaaa  120
tgcaactatt tctatgtaaa tttaatatta gatatttata cat                  163

SEQ ID NO: 3              moltype = DNA   length = 539
FEATURE                   Location/Qualifiers
source                    1..539
                          mol_type = genomic DNA
                          organism = Homo sapiens
SEQUENCE: 3
gactacacca tgaggcctta ttacagtgtt agtttgttct gacaaatgcc atgcgtattt   60
ttaagaacct aaacatgctt ctgaagctta atagacaaaa gcctcttaag gaaaaaaaga  120
aaagcactgt tgaagtcatg tacttctgtt aaaatcatag cctctctttt agacatattt  180
atgcttctgc ttacattttt agattttatt acttgttagt aatttggata gaatcattca  240
gagttgtaaa ttcaggtagt aatagaacta ctcaattttt ccaactgtct gtttagaaaa  300
gctttttttt ttgcattctt tatgtttatt tatttaaaat gcaactattt ctatgtaaat  360
ttaatattag atatttatac ataaaagaca acatggtagt ataatgacat catattcttt  420
tactgtttca tttgaaaatt acaaagataa tatctttagt tgattttgtc acagatacat  480
attattttta atataccaag aacagaactt atatattaat aaaaatcctt tggaaagct   539

SEQ ID NO: 4              moltype = DNA   length = 190
FEATURE                   Location/Qualifiers
source                    1..190
                          mol_type = genomic DNA
                          organism = Homo sapiens
SEQUENCE: 4
cgctctcagc tctcggcgca gtatgactcc atgaagggca aggggacgcg agataaggtc   60
ctgatcagaa tcatggtctc ccgcagtgaa tctacacccc caagtgcata tgggtctgtc  120
aaagcctata ctaactttga tgctgagcgg gatgctttga acattgaaac agccatcaag  180
accaaaggtg                                                       190

SEQ ID NO: 5              moltype = DNA   length = 190
FEATURE                   Location/Qualifiers
source                    1..190
                          mol_type = genomic DNA
                          organism = Homo sapiens
SEQUENCE: 5
```

-continued

```
cgctctcagc tctcggcgca cggcccagct tccttcaaaa tgtctactgt tcacgaaatc   60
ctgtgcaagc tcagcttgga gggtgatcac tctacacccc caagtgcata tgggtctgtc  120
aaagcctata ctaactttga tgctgagcgg gatgctttga acattgaaac agccatcaag  180
accaaaggtg                                                         190
```

SYNTHETIC GENOMIC VARIANT-BASED SECURE TRANSACTION DEVICES, SYSTEMS AND METHODS

RELATED PATENT APPLICATIONS

This application is a continuation of U.S. application Ser. No. 18/084,449 filed Dec. 19, 2022 which is a continuation of U.S. application Ser. No. 17/707,925 filed Mar. 29, 2022 which is a continuation of U.S. application Ser. No. 16/034, 271 filed Jul. 12, 2018 which claims priority to U.S. provisional application 62/045,062 titled "Genome-Based Transaction Devices, Systems, and Methods", filed Sep. 3, 2014. U.S. application Ser. No. 14/844,974 also claims priority to and also has subject matter that relates to co-pending U.S. provisional application 62/057,922 titled "Genome-Based Transaction Devices, Systems, and Methods", filed Sep. 30, 2014; U.S. provisional application 62/062,023 titled "Transaction Cards, Devices, Systems, and Methods", filed Oct. 9, 2014; U.S. provisional application 62/077,683 titled "Financial Service Discovery via Healthcare Transactions, Device, Systems, and Methods", filed Nov. 10, 2014; and U.S. provisional application 62/137,129, titled "Security Using Synthetic Genomic Variants, Devices, Systems and Methods, filed Mar. 23, 2015. These and all other extrinsic references referenced herein are incorporated by reference in their entirety.

This application contains a Sequence Listing in electronic format. The Sequence Listing file, titled N1077.10051US06_SequenceListingST26.XML, was created on Oct. 4, 2024, and is 7 kilobytes. The information in electronic format of the Sequence Listing is incorporated herein by reference in its entirety.

FIELD OF THE INVENTION

The field of the invention is genome-based digital security technologies.

BACKGROUND

The background description includes information that may be useful in understanding the present invention. It is not an admission that any of the information provided herein is prior art or relevant to the presently claimed invention, or that any publication specifically or implicitly referenced is prior art.

With the continued growth of the myriad digital accounts with which consumers must engage, consumers are faced with the problem of managing passwords, keys, or other tokens for securely accessing such accounts. The problem is not limited to just token management. Rather, the problem also extends into other forms of authentication or authorization for accessing consumer data (e.g., electronic medical records, social media, etc.).

Consumers continue to encounter a growing complexity of managing electronic or digital accounts. For example, a consumer may easily have dozens of financial accounts, perhaps even a dozen individual accounts with a single institution. Still further, the consumer might also have dozens or even hundreds of on-line accounts for various services: games, on-line retailers, social networks, email, or other accounts for example. Such problems are exacerbated by the explosion of new transaction services or data feeds made available to consumers for their various accounts or from new vendors. Consumers lack mechanisms by which they can discover new services and integrate such services into their daily lives with ease in view of the cacophony of digital accounts the consumers already have.

One specific area in which consumers encounter numerous account management problems includes the healthcare arena. In the healthcare arena, a consumer might have their electronic medical records or health records stored within numerous accounts spread across numerous healthcare institutions; for example, hospitals, insurance companies, dentists, specialists, primary healthcare physicians, or other healthcare entities. Unfortunately, the consumers often lack access to their data located on the remote servers of the entity storing the data. Thus, especially in healthcare, consumers not only suffer because they lack access to their own data but also suffer because it is impossible for the consumer to manage so many accounts even beyond the healthcare markets.

Thus there remains considerable need for transaction devices, systems, and methods by which consumers could manage numerous accounts, discover new services, and ingest new electronic transaction services into their lives via a simple technique.

Others have put forth effort toward systems through which consumers are able to securely access data through a common system. For example, Microsoft® offers consumers access to their Passport™ services, which allows consumers to access multiple, disparate web sites through a single login. In addition, many on-line web sites also allow users to access their services based on other site logins; Google or Facebook® logins for example. Although useful, the consumer is still required to remember their passwords. Further, the passwords generated by consumers can be easily hacked or guessed.

With the growth of communication technologies, especially cell phones, there has been movement toward using cell phones as a personalized hub of information. However, such devices lack sufficient life spans to function as a solid personalized identification system. Ideally, consumers would have access to a mechanism through which they could interact with data stores, data custodians, or other intelligent systems in a high personalized manner. What has yet to be fully appreciated is that consumers or other types of individuals could use their own genomic information to interact with myriad types of computing systems where the individual's genomic information provides for highly personalized transactions. Thus, there remains a need for personalized, genome-based transaction devices, transaction servers, or transaction systems.

Systems have been described that offer consumers access to biometric authentication systems, which aid in personalizing a user's key. For example, U.S. patent application 2013/0307670 to Ramaci titled "Biometric Authentication System", filed May 13, 2013, discusses a biometric authentication system. A user's cell phone could store a user's biometric information (e.g., finger print, EKG signature, etc.), which can be used as a key. Interestingly, Ramaci states that one could access genomic database on using their disclosed techniques, but fails to appreciate devices, systems and methods set forth in the present invention.

In a somewhat similar fashion, U.S. patent application publication 2010/0121872 to Subramaniam titled "Personally Controlled Storage and Testing of Personal Genomic Information", filed internationally on Mar. 27, 2008, discusses a portable storage device that can store a person's genomic information. Although the storage device could be a USB device and could store genomic information, Subramaniam also fails to appreciate devices, systems and methods set forth in the present invention that may be used in a secure transaction system.

U.S. patent application publication 2002/0129251 to Itakura et al. titled "Method and System for Individual Authentication and Digital Signature Utilizing Article having DNA Based ID Information Mark", filed May 17, 2001, describes a method of using a person's DNA mixed with ink along with a recording medium storing genome related information as a means for authenticating the person. Similarly, U.S. patent application publication 2014/0074696 to Glaser titled "Credit Card Form Factor Secure Mobile Computer and Methods", filed Sep. 9, 2013, also describes a device where a genome can be used interchangeably as one would use a finger print, or retinal scan, except in a credit card format.

Use of a person's genome as a security measure or as personal identification has previously presented numerous problems. One major problem relates to keeping a person's genome information secure. A threat (e.g., a malicious person or entity) could easily obtain a tissue sample from the person without much difficulty. For example, the threat could simply obtain ambient skin flakes or hair follicles even without the person knowing their tissues have been compromised. In such circumstances, the threat could analyze the tissue samples to obtain a whole genome sequence (WGS) of the person. The threat can then use the WGS of the person to assume the person's identity especially in situations where the WGS data is used as a key in a digital transaction setting.

Glaser posits that a genome could be used interchangeably as one would use their name, social security number, driver's licenses, or other ID. However, as stated above, in the Glaser approach a threat could merely obtain a tissue sample from a person in order to gain sufficient information to represent themselves as the person.

A more ideal approach would improve on the genomic information to ensure that the secure genomic information remains intimately linked to the person even in view of threats gaining access to an unauthorized tissue sample. Thus, there remains a need for devices, systems, or methods that further secure the identity of individuals based on genomic information.

SUMMARY

The inventive subject matter provides apparatuses, systems and methods in which genomic information can be leveraged for security purposes while also ensuring that the genomic information remains intimately linked to the corresponding entity. The genomic information can be further secured through the use of a synthetic variant; a computer generated variant that appears to be a natural part of the person's genome but is not actually or naturally part of the genome. The synthetic variant can be inserted into the person's genome data stored on a transaction device as well as stored on remote servers that are configured to validate transactions. One aspect of the inventive subject matter includes a genome-based security device (e.g., smart card, cell phone, smart watch, smart home, etc.). The security device includes a memory, a processing unit (e.g., CPU, multi-core CPU, etc.), a communication interface configured to couple with one or more external devices, and a security engine. The memory comprises a non-transitory computer readable medium (e.g., RAM, flash, HDD, SSD, etc.) that is configured to store digital genomic data associated with a biological entity. The digital genomic data includes at least one synthetic variant that is generated to be substantially unique to the biological entity. The synthetic variant is synchronized with similar information on a remote digital security server. The security engine is executable on the processing unit according software instructions stored in the memory and configures the processing unit to execute steps to fulfill security roles or responsibilities. The security engine maintains synchronization of the synthetic variant with respect to synthetic variant data on a remote digital security server. For example, the synthetic variant on the security device might rotate through values based on a time-based secured function at the same time the same data is rotated on the server according to the same function. The engine further couples with one or more external devices, a point of sales device for example, via the communication interface. The security engine further exchanges at least the synthetic variant with the external device, which in turn causes the external device to participate in a digital transaction. The external device could be the remote security server or could be a point-of-transaction device (e.g., card reader, kiosk, etc.). The remote server can authorize the transaction as a function of the genomic data and the synthetic variant. Example transactions can include financial transactions, commercial transactions, protocol transactions, healthcare transactions, or other types of transactions.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

For the purposes of illustration only, several aspects of particular embodiments of the invention are described by reference to the following figures:

FIG. 2 illustrates an exemplary partition of genomic data showing a difference section 231 marked as SEQ ID NO: 2 within digital genomic data 235 marked as SEQ ID NO: 3 that can implement a genomic data-based transaction in accordance with an embodiment of the present invention;

DETAILED DESCRIPTION

Figure 1:
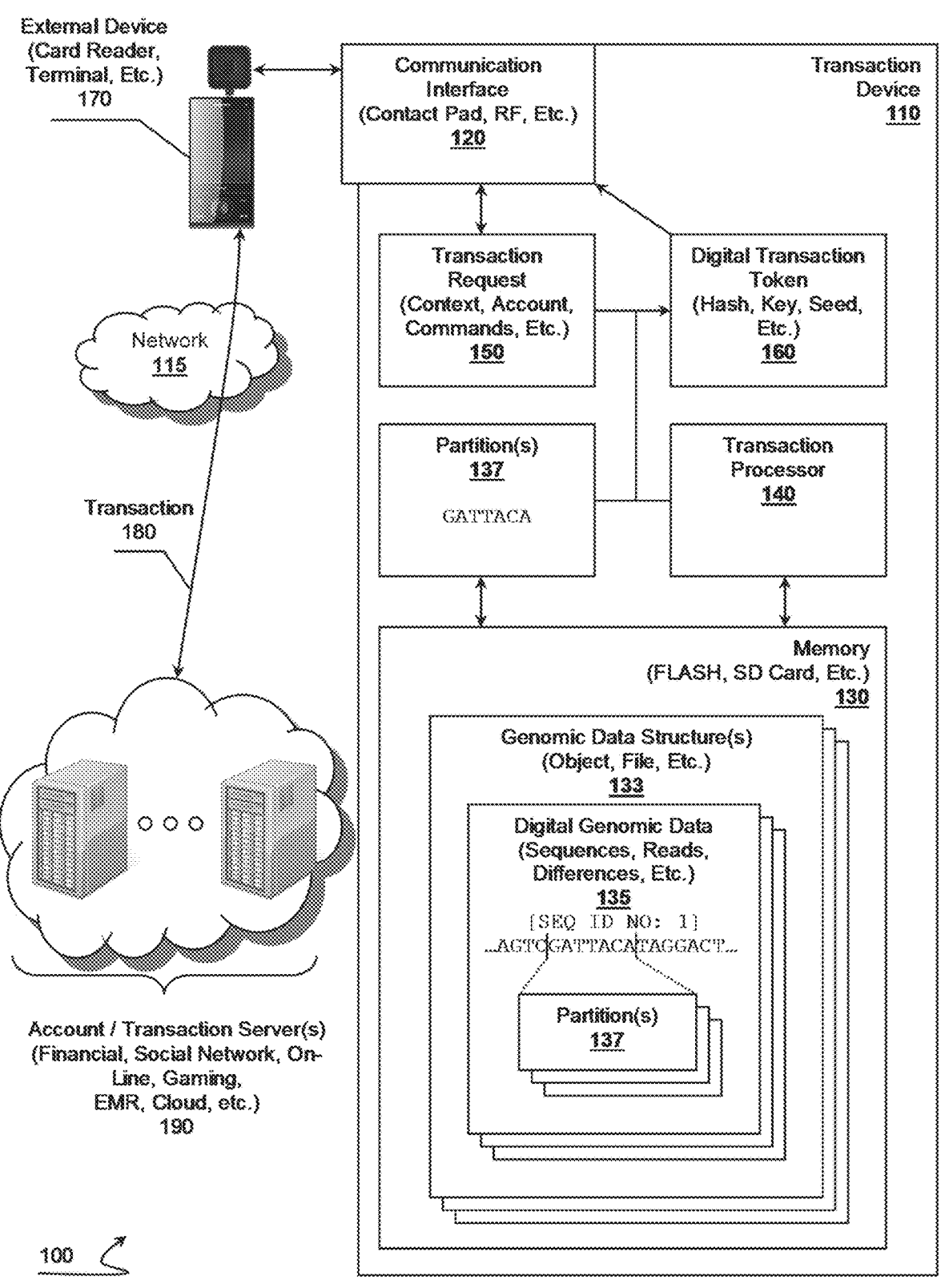
FIG. 1 illustrates a block diagram of an exemplary distributed computer system including an exemplary transaction device using digital genomic data 135 marked as SEQ ID NO: 1, and partition 137 of the digital genomic data 135 that can implement one or more aspects of a genomic data-based transaction system or method according to an embodiment of the present invention.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, PLA, PLD, FPGA, etc.). The software instructions preferably configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, when a system, engine, module, device, server, or other computing element is described as configured to perform or execute functions on data in a memory, the meaning of "configured to" or "programmed to" is defined as one or more processors being programmed by a set of software instructions stored in the memory of the computing element to execute the set of functions on target data or data objects stored in the memory.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The focus of the disclosed inventive subject matter is to enable construction or configuration of a computing device to operate on vast quantities of digital data, beyond the capabilities of a human. Although the digital data represents genome data, it should be appreciated that the digital data is a representation of one or more digital models of genomic-data, not a genome itself. By instantiation of such digital models in the memory of the computing devices, the computing devices are able to manage the digital data or models in a manner that provides utility to a user of the computing device that the user would lack without such a tool. Further, without configuration or programming of the computing devices, the computing devices would not be able to manage such data objects.

The disclosed inventive subject matter represents a transaction device network environment, referred to here as a transaction device ecosystem, which leverages at least one entity's genomic information as a foundation for enabling a transaction. The entity's entire genome can be stored in the memory of the device and segmented into partitions having a corresponding security strength; a cryptographic strength for example. The strength of the partition may be an inherent strength based on the encoded information or may be a strength measured relative to other members of a population (e.g., race, gender, community, family, etc.). One or more partitions can be used to generate a digital transaction token; a key or password for example, which can enable a transaction. The digital transaction token may be used for many different types of transactions possibly including accessing an account, a financial transaction, a protocol authentication, an authorization, transfer of data, storage of data, interaction among computing devices (e.g., API, cloud services, web services, image matching or classification, etc.), co-payments, check-in or registration, loyalty card transactions, incentive program transaction, reward program transactions, or other types of interactions.

FIG. 1 illustrates a transaction device network environment, referred to here as a transaction device ecosystem 100 where transaction device 110 enables external device 170 (e.g., PoS terminal, docking station, portal, cell phone, appliance, kiosk, gas station pump, dumb terminal, etc.) to conduct one or more of transaction 180, possibly with remote account servers 190 over network 115 (e.g., Internet, PSTN, cellular network, LAN, VPN, WAN, PAN, etc.). Transaction device 110 is a computing device having communication interface 120, non-transitory computer readable memory 130, and transaction processor 140. Memory 130 is configured or programmed to store software instructions that cause transaction processor 140 to execute numerous steps that fulfill the roles or responsibilities discussed below. Transaction device 110 can be further provisioned with one or more embedded operating systems to provide underlying operating system services (e.g., threading, file system, device drivers, memory management, hypervisors, communication stacks, etc.). Example suitable operating systems include QNX®, VxWorks®, embedded Linux, or other operating systems.

Communication interface 120 represents sufficient physical elements by which transaction device 110 is able to exchange data with external device 170. In some embodiments, where transaction device 110 comprises a credit card form factor, communication interface 120 may include a contact pad having multiple electrically conducting elements. Other form factors might have other, different types of interfaces. For example, in a mobile device form factor (e.g., cell phone, gaming console, etc.), communication interface 120 may include a wired interface (e.g., USB interface, Ethernet interface, serial interface, etc.), or even a wireless interface (e.g., antenna, RF induction interface, near field communication interface, WiGIG interface, Bluetooth® interface, 802.11 interface, etc.).

In some embodiments, communication interface 120 comprises a high bandwidth, near field communication device capable of transferring large amounts of data in a few seconds. For example, communication interface 120 may comprise one on more chips as described in U.S. Pat. No. 8,554,136 to McCormack titled "Tightly-Coupled Near-Field Communication-Link Connector-Replacement Chips", filed Dec. 21, 2009; U.S. Pat. Nos. 8,714,459 and 8,757,501 to both to McCormack et al. and titled "Scalable High-Bandwidth Connectivity" filed May 14, 2012 and Mar. 4, 2013 respectively; U.S. Pat. No. 8,811,526 to McCormack et al. titled "Delta Modulated Low Power EHF Communication Link", filed May 31, 2012; and U.S. patent application publication 2014/0273856 to Kyles et al. titled "Extremely High Frequency Systems and Methods of Operating the Same", Mar. 13, 2014. The chip described by these references is able to transfer a gigabyte of data in less than 2 seconds over distance of a few centimeters. Thus, a whole compressed genome of size 800 MB, for example, may be transferred to external device 170 in just over a second.

In view that transaction device 110 can take on a credit card form factor, it should be appreciated that transaction device 110 can comprises nearly any type of card. Example types of cards that may leverage the disclosed techniques include healthcare cards, loyalty cards, driver's licenses, credit cards, or other types of cards. It is also possible that transaction device 110 may take on other forms beyond a standard credit card form factor. For example, transaction device 110 may also comprise a passport form factor, a mobile or smart phone form factor, a robotic assistant, or other type of form factor.

Transaction processor 140 comprises a computer chip coupled with memory 130 and communication interface 120. Transaction processor 140 executes software instructions stored in memory 130 to fulfill the roles or responsibilities discussed herein. Example computer chips that can be leveraged include ASICs, RISC chips, ARM, x86, GPU, FPGA, or other type of chip. For credit card form factors, low powered chips that can be powered via communication interface 120 or a battery would be more preferable. In some embodiments, transaction processor 140 can also include one or more cryptographic support chips or modules in support for providing secure functions (e.g., encryption, decryption, hashing, etc.).

Memory 130 comprises a digital storage medium, preferably a persistent storage medium, capable of storing large quantities of digital genomic information as well as software instructions. Examples of suitable memory include FLASH, ROM, SSD, HDD, RAM, DRAM, or other types of memory. In some embodiments, memory 130 may comprise one or more removable media. For example, memory 130 may comprise a removable micro SD card such as those offered by San Disk® or Lexar®. Readily available micro SD cards can be obtained in various memory capacities where more capacity is generally more preferable subject to cost constraints. Example capacities of SD cards include 4 GB, 8BG, 16 GB, 32 GB, 64 GB, 128 GB, 256 GB, or more. In some embodiments, memory 130 adheres to one or more secure memory standards (e.g., FIPS 140-1, FIPS 140-2, FIPS 140-3, etc.) to protect the contents of memory 130. Consider a case where digital genomic data 135 is considered highly sensitive. In such a case, memory 130 may adhere to FIPS 140-2, level 4, where memory 130 and its contents may be considered as part of the cryptographic module of transaction device 110. Should a physical intrusion occur or be detected, the contents of the memory can be zeroed or otherwise destroyed.

Memory 130 stores one or more of genomic data structures 133 having digital genomic data 135 representative of an entity's genome. Although the entity may comprise any object having genetic information, in exemplary embodiments, the entity should be considered a mammal and more particularly a human. Thus, digital genomic data 135 may be a person's genomic information, which can be used to authentic or authorize transactions 180. Genomic data structures 133 may take on different forms depending the nature or structure of digital genomic data 135. In some embodiments, genomic data structures 133 may be instantiated data objects in memory 130 comprising one or more application program interfaces (APIs) through which digital genomic data 135 may be accessed. For example, genomic data structures 133 may represent individual chromosome objects, each chromosome having its own API, where each chromosome object may be considered a standalone database, which may be stored individually in separated secured containers (e.g. encrypted file systems, etc.). In other embodiments, genomic data structures 133 may be a file system where digital genomic data 135 or partitions 137 may be files in the file system. Genomic data structures 133 may comprise a portion of the entity's genome information or may comprise an entity's whole genome, perhaps spread over multiple data objects.

Digital genomic data 135 represents an encoding of a person's genomic data. As illustrated, the genomic data may be an encoding of their DNA as a sequence of base pairs. Typically a human's whole genome includes about 3,000,000,000 base pairs. Naively assuming one byte for each pair, then digital genomic data 135 may consume, in aggregate across all genomic data structures 133, about 3 GB. Still, the sequences may be stored according to one or more formats depending on how much of the data is to be stored. If the memory capacity is tight, each base pair may be encoded in bit-wise values where only two bits are required to store the four possible base pair configurations (i.e., A-T, T-A, C-G, and G-C). Such a storage format would allow the 3B base pairs to be stored in about 800 MB, but would require additional data processing to access or unpack the data.

In view that memory modules having large memory capacities are relatively inexpensive, extreme compression is not considered a requirement. Rather, digital genomic data 135 can be stored according to one or more known standard formats to ease data access and data processing. Example standard formats may include FASTA, FASTQ, BAM, SAM, VCF, BED or other formats. It also possible to store digital genomic data 135 in other proprietary formats, possibly including GAR format offered by Genalice® or BAM-BAM by NantOmics, LLC. In some embodiments, memory capacity can be conserved by using a compressed format where one or more portions of the data are compressed if they are not accessed frequently (e.g., quality scores might be compressed, etc.). Given the memory capacity constraints of memory 130, genomic data structure 133 would likely be less than 200 GB, 100 GB, 90 GB, 50 GB, 5 GB, or 1 GB in size to fit within the capacity of memory 130. For example, in an embodiment where genomic data structure 133 operates as a single file system within a 128 GB micro SD card, then the size of files aggregated in the file system would be less than 128 GB, possibly around 100 GB to preserve a 28 GB work space, if necessary.

Memory 130 further stores one or more of partitions 137 of digital genomic data 135. Partition 137 may be an instantiated data object that subtends a portion or portions of a genomic sequence. As shown in FIG. 1, partition 137 is represented by the sequence "GATTACA", which is a substring in a larger sequence from digital genomic data 135. Typically, partition 137 may also include data members that reflect the position of the corresponding strings; a start location, an end location, lengths of the strings, security strength of the strings, cryptographic strength of the strings, a partition identifier, or other parameters. Partition positions and/or lengths can be defined based on, e.g., the University of California-Santa Cruz genome browser coordinate system. Additional details regarding partitions are discussed with respect to FIG. 2.

Transaction processor 140 has multiple responsibilities within transaction device 110. Upon execution of corresponding software instructions stored in memory 130, transaction processor 140 is configured or programmed to identify one or more partitions 137 of genomic data structure 133 based on transaction request 150. Transaction request 150 comprises data or a communication received via communication interface 120 and relating to transaction 180. In some embodiments, transaction request 150 might include commands or signals generated from external device 170. For example, in embodiments where transaction device 110 comprises a credit card form factor and communication interface 120 comprises a contact pad, NFC chip set, external device 170 (e.g., a card reader, NFC terminal), can submit commands to transaction processor 140. In other embodiments, transaction request 150 can comprise transaction data submitted to transaction device 110. The transaction data can include context data possibly comprising a location, a time, a transaction identifier, an account identifier, a user identifier, an external device identifier, an event (e.g., new event, local event, life event, etc.), a user preference, a protocol identifier, public key information, a password, a routing number, account information, genomic partition information (e.g., desired strength, location, length, etc.), a cryptographic suite, or other information in support of transaction 180. The context data may also be derived from sensor data obtained from one or more sensors (not shown) coupled with or integrated into transaction device 110. Example sensors may include a GPS sensor, a biometric sensor, a camera, a pulse OX sensor, a microphone, a touch-sensitive display, a key pad, a key board, or other type of sensor.

Transaction processor 140 can identify partitions 137 through numerous techniques. In some embodiments, partitions 137 may be predefined and stored in a local partition database (not shown; e.g., files, lookup table, etc.) in memory 130, which is configured to store many partitions 137, wherein the partitions 137 may be indexed by transaction attributes. For example, transaction processor 140 can derive one or more transaction attributes from transaction request 150 or associated context data. Example transaction attributes may include an account number, identifier of external device 170, identifier of account servers 190, or other information. Transaction processor 140 using the attributes to query the partition database to select one or more of partitions 137 from the partitions 137 that are available. In other embodiments, transaction processor 140 may build partition 137 based on the transaction attributes. Should transaction request 150 provide an indication of a desired security strength for the transaction, then transaction processor 140 may create a new partition 137 having the required features.

Transaction processor 140 is further configured or programed to derive digital transaction token 160 from digital genomic data 135 within partition 137. In the example shown, digital transaction token 160 would be generated or derived from the sequence "GATTACA". It should be appreciated that digital transaction token 160 is derived in manner that is complementary to the protocol associated with transaction 180. For example, in a PKI system, digital transaction token 160 might comprise a private key or public key derived from the genomic data within partition 137. In other scenarios, digital transaction token 160 may include a hash derived from partition 137. Example hash functions may include MD5, SHA-1, SHA-2, SHA-3, RIPEMD, Whirlpool, Scrypt, or other known hash functions, or hash functions yet to be developed. Further, digital transaction token 160 may comprise encrypted data from a message where the message is encrypted based on a key derived from partition 137. Example cryptographic algorithms that may be used to create digital transaction token 160 may include AES, DES, 3DES, or other cyphers. Still further, digital transaction token 160 may represent a pseudo-random number generator seed, perhaps in support of a video game; or may be an actual pseudo-random number itself generated based on such a seed. Even further, digital transaction token 160 may comprise the genomic sequence itself assuming it has a sufficient length or other characteristics. In such cases, the genomic sequence may be converted to a desired format, such as ASCII or binary data for example. Within the context of cryptocurrencies, digital transaction token 160 may comprise a wallet address or even a nonce in support of validating transaction blocks in a blockchain (e.g., BitCoin blockchain, LiteCoin blockchain, etc.).

It should be appreciated that digital transaction token 160 can be generated in real-time or may be generated beforehand and stored in memory 130. The advantage of deriving digital transaction token 160 in real-time allows transaction device 110 operate in a wide variety of use cases, possibly where external device 170 provides instructions to transaction device 110 on the security needs or requirements for transaction 180. Storing previously generated digital transaction tokens 160 reduces latency on transactions, especially application specific use cases (e.g., healthcare transaction cards, loyalty cards, e-wallets, etc.).

Transaction processor 140 can be further configured or programmed to enable electronic transaction 180, in response to transaction request 150, with external device 170 as a function of the digital transaction token 160. For example, external device 170 might request a key to access one or more account servers 190, perhaps associated with a financial account. In response, transaction device 110 constructs digital transaction token 160 to operate as the key, possibly in an encrypted format. Transaction processor 140 delivers digital transaction token 160 to external device 170 via communication interface 120. In a more specific example, transaction request 150 may comprise a transaction key associated with external device 170 or account servers 190, possibly a public key of external device 170. In response, digital transaction token 160 may comprise a private key of transaction device 110, which can be used for further communications as part of a PKI communication system.

Transaction 180 is illustrated as taking place between account servers 190 and external device 170 over network 115. This example is for illustrative purposes only, and should not be considered restrictive. Rather, it is also possible that transaction 180 might only be between external device 170 (e.g., an ATM, computer, etc.) and transaction device 110 (e.g., cell phone, bank card, etc.). Thus, transaction 180 may represent any of a broad spectrum of possible transaction types depending on the nature of the target use case. Example transactions may include financial transactions, a protocol transaction (e.g., SSH, SSL, etc.), a web service or API access, a database transaction (e.g., login, logout, query, etc.), an interaction with external device 170 (e.g., command, control, etc.), an authorization, an authentication, an encryption, a decryption, or other type of transaction. In view that transaction device 110 can exist within a larger transaction ecosystem 100 leveraging various protocols, transaction processor 140 can be further configured or programmed to exchange data with external device 170 via a secured protocol (e.g., SSL, SSH, etc.). Additional example protocols that can be used to support transaction 180 may include character-level transmission protocol (e.g., T=0 protocol), a block-level transmission protocol (e.g., T=1 protocol), a secured socket layer protocol, an encrypted protocol, APDU transmission protocol, or other secure protocols.

In many embodiments, transaction 180 is associated with one or more accounts, possibly managed by account servers 190. In such scenarios, partitions 137 can map to the accounts. This approach is considered advantageous because it allows a consumer to create account-specific partitions 137 based on the genomic data without requiring the consumer to generate or remember numerous individual passwords. Example accounts to which partitions 137 may map include financial accounts, web site accounts, computer accounts, mobile device account, social media accounts, bank accounts, credit card accounts, electronic medical accounts, benefits accounts, loyalty program accounts, gaming accounts, college or educational accounts, or other types of accounts. Account servers 190 would also have access to authentication information in order to finalize any required authentications or authorization either locally stored or perhaps based on a service (e.g., certificate authority, RADIUS, Kerebos, etc.)

It should be further appreciated that the above described techniques can be enhanced by binding information from partitions 137 with additional data to secure the nature of detail transaction token 160. For example, a consumer may provide a personal identification number (PIN) that can be hashed with the genomic sequence of partition 137 to give rise to digital transaction token 160. Such an approach aids in further securing the information in case the genome information is exposed. Further, biometric information may be used to further secure transaction device 110. A biometric sensor (e.g., camera, fingerprint scanner, etc.) can be integrated with or coupled to transaction device 110. The biometric sensor data can also be used in combination with partition 137 (e.g., hash, etc.) to derive digital transaction token 160.

In more interesting embodiments, partitions 137 are considered dynamic and can change with time. As time passes, a partition 137 may shift position, size, rotate, shape, arrangement, motifs, or other property. More specifically, partitions 137 should shift their properties according to a secret, pseudo-random function operating based on a known seed and a current time. Account servers 190 would likely be aware of the same function, seed, and time so they remain in synch with the states of partitions 137. In such embodiments, transaction device 110 would comprise a timer or access to accurate time information, perhaps from GPS information.

Transaction device 110 can comprise different form factors. A more preferred form factor comprises a housing sized and dimensioned to adhere to a credit card form factor. For example, transaction device 110 may adhere to ISO/IEC 7810. The housing would house at least memory 130 and transaction processor 140. Still, in other embodiments, transaction device 110 may comprise a smart phone or other type of mobile device (e.g., PDA, game device, sales terminal, kiosk, etc.).

Transaction device 110 can also include one or more displays (not shown) to facilitate user interaction with the device. In some form factors, the display may comprise an LED or LCD display. In other form factors, the display may comprise an e-ink display or e-paper display. Providing a display aids in allowing the user to select among partitions, accounts, digital tokens, or other user selectable items that are presented via the display.

FIG. 2 provides additional details regarding the nature of partitions with respect to genomic data. Digital genomic data 235 represents one or more encodings of genomic data. In this example, digital genomic data 235 represents an ASCII representation of a DNA sequence. As discussed previously, digital genomic data 235 may include an entity's whole genome; about 3 billion base pairs, which would require about 3 GB if stored as one byte per base pair. Still, it is possible in some embodiments to store genomic differences relative to a reference genome. For example, rather than storing all of a genome, the transaction device may store only differences 231 that are distinct from a reference genome. The example sequence presented in FIG. 2 is selected from gene PCNX (pecanex homolog (*Drosophila*)) located on chromosome 14, which starts at position 70,907, 405 and ends at 71,115,385, with a length of 207,978.

Although digital genomic data 235 is presented as a DNA sequence, digital genomic data 235 may also include other types of genome information. In various embodiments, digital genomic data 235 may represent a whole genome as discussed previously, an exome, a transcriptome, a proteome, a protein pathway, mitochondrial DNA, telomeres, or other types of genetic information and/or associated metadata. Further, digital genomic data 235 might represent different tissues (e.g., a tumor, healthy tissue, diseased tissue, an organ, etc.). Even further, digital genomic data 235 might represent the tissue at different points in time (e.g., age, periodical samples, etc.). In such embodiments, digital genomic data 235 may comprise multiple complete instances of a whole genome, or multiple different instances where each instance represents a snapshot in time. For example, digital genomic data 235 may include multiple instances of differences from a reference genome where the differences are measured or otherwise determined every year.

Digital genomic data 235 can also include information beyond sequences. In some embodiments digital genomic data 235 can also include metadata that describes the nature of the genomic data itself, how it was captured, or other information. For example, if digital genomic data 235 is stored in a SAM or BAM format, metadata might include alignment information for sequences (e.g., linear alignments, chimeric alignments, read alignments, etc.), reads, coordinates, insertions, deletions, soft or hard clipping, or other information. Additionally, digital genomic data 235 might include genetic metadata relating to the nature of the sequences, possibly including gene names, gene coordinates, short tandem repeats (STRs), single nucleotide polymorphisms (SNPs), variations, mutations, codon bias, exon-intron boundaries, exon or intron placements, exon or intron lengths, telomeres information, regulatory sequences, RNA coding genes, centromeres, arrangements or placements of one or more of the previous features, or other metadata that describes features of the sequences. It is specifically contemplated that such metadata can be integrated into partitions 237 as part of the genomic data that is used to derive a corresponding digital transaction token.

Differences 231 are represented as bold, underline characters; although the sequence listed is not actually a difference with respect to the PCNX gene. For example, information about differences 231 may include location, lengths, or other coordinate information relative to the reference genome. In view that large memory capacity chips are cost effective for deployment in transaction devices, differences 231 can also be stored or flagged along with the whole genome to which they are bound. The reference genome may be a standardized genome, an average genome across a population (e.g., demographic) or within a family, or other construct.

In the example shown in FIG. 2, partitions 237 are instantiated based on the nature of differences 231. Partitions 237 can be instantiated to encompass at least a portion of difference 231. This approach ensures that the genomic data used for security is unique to the individual. Alternatively, differences 231 might be unique to a larger population, a family or demographic for example. The level of "uniqueness" of differences 231 can be used to provide for security or access levels across a population. Thus, partitions 237 may indicate a security level to which a user or individual is entitled. Further, partitions 237 can also encompass common portions of the reference genome, allowing for scaling the relative strength of partition 237 with respect to a role in a security ecosystem.

Partitions 237 may encompass a sequence that is considered a hapax legomenon within the genome. A hapax legomenon represents sequences of nucleotides that only appear once within a corpus of genomes (i.e., one or more genomes) and thereby represents unique information for that specific corpus. Further, such hapax legomenons may also be measured with respect to a corpus of genomes across a population (e.g., a family, a demographic, a race, etc.), which would indicate that an individual's hapax legomenon would further differentiate the individual from others in the population.

Partition 237 is represented as an instantiated data object having multiple data members. It also possible that partition 237 may comprise corresponding APIs or methods that allow the transaction device to gain access to the information stored within partition 237 or otherwise manage partitions 237. Such APIs may include createPartitiono, deletePartitiono, readPartitiono, writePartition(      ), unlockPartitiono, or other APIs. Partition 237 includes a partition identifier, which is represented by a GUID. However, other identifying schemes may also be employed. For example, the partition identifier might follow a hierarchical namespace indicating how or under which circumstances the partition is to be used. For the sake of discussion, partition 237 is assumed to be the entire PCNX gene. Thus, the information about the genomic sequence in partition 237 corresponds to the PCNX location, start, end, and length.

The length or nature of sequences associated in partitions 237 can vary substantially based on a target need or requirement. Further the sequence length may be measured using different units of genomic primitive elements. In some embodiments, the primitive elements might be base pairs while in other embodiments, codons might represent the fundamental unit of measurement. Still, the partition 237 might represent no more than 1M elements, 500K elements, 100K elements, 50K elements, 10K elements, or no more than 1000 elements. Thus, the size and nature of genomic information in partitions 237 can be scaled to fit a target need.

Interestingly, the genomic information in partition 237 is not necessarily required to be a linear sequence. It is also possible that partition 237 may represent other structural forms. For example, rather than using a linear sequence, the genomic data might be selected from block 238 where columns are read from left to right. Some data formats, such as FASTA, are amenable to block level reading. Further, the genomic data may be selected pseudo-randomly from within digital genomic data perhaps based on a user's secret PIN. Thus, partitions 237 can be synchronized (e.g., changed, shifted, rotated, etc.) with account servers according to one or more time-based synchronization functions. Consider a scenario where digital genomic data 235 is stored in FASTA format where the sequence is represented by ASCII characters as a large block of text. Block 238 may represent a sliding window that overlays the block of text; those letters falling within the window may be the token. The sliding window may shift up, down, left, right or any direction with time according to the time-based synchronization functions.

Partitions 237 can also comprise a difference measure indicating how different the genome sequence is relative to the reference genome. The difference measure aids in determining how secure the sequence would be for various security proposes. The difference measure may comprise a ratio of the number of base pair differences relative to the total number of base pairs in the sequence. The higher the difference measure, the more secure the sequence would be relative to similar sequences of other entities. However, differences do not necessary equate to robustness or strength. Still, partitions 237 can be selected for use based on the difference measure, as required by a transaction request or protocol.

A security strength of partition 237 can be determined through different techniques. One possible approach is to measure information entropy in the sequence, preferably including differences 231. A high information entropy, Shannon entropy for example, would indicate the sequence tends toward a more random nature, which is considered more difficult to break. Such a security measure can be used with respect to using partition 237 as a key, password, or other type of token. The entropy of the sequence can be derived from the digital representation of the sequence, a binary packed representation, or other encoding. A cryptographic strength of partition 237 can be derived taking into account an implementation of a target cryptographic algorithm (e.g., AES, DES, 3DES, Hash function, etc.).

Partitions 237 can be compiled into partition database 250 stored within the memory of the transaction device. For ease of discussion, partition database 250 is presented as a look up table. Partition database 250 indexes partition identifiers 255 based on accounts 253 as an example. It should be appreciated that partition identifiers 255 may also be indexed by other transaction context information. Accounts 253 represent the electronic accounts to which a user has bound one or more partitions 237. When the transaction device receives a transaction request for an account, the transaction device can consult partition database 250 to determine the partition identifier 255 (e.g., GUIDs, UUIDs, etc.) of which partition 237 should be used in enabling the transaction. The transaction device uses the identifier to find the corresponding partition 237.

Partition database 250 can also provide a mapping of available partitions to their respective security strengths. This allows the transaction device to provide digital transaction tokens having required features based on partitions 237. For example, a user might wish to setup a new user account, perhaps as part of a medical records exchange that requires strong security. The user can submit a transaction request to the transaction device. In response, the transaction device finds a partition, or instantiates a new partition, having the desired security strength (e.g., high entropy, large differences from a reference genome, etc.). This allows the transaction device to select partitions 237 based on strength, difference measures, or other factors.

The disclosed genome-based secure, transaction system can operate in a larger healthcare ecosystem. In some embodiments, the disclosed techniques of mapping genome partitions to security or cryptographic strengths can be used to authenticate a user or to authorize access to electronic medical data across a clinical operating system. One example clinical operating system includes cOS™ offered by Nant Health, LLC (see URL www.nanthealth.com). As stakeholders interact with the cOS services, the genomic partitions within their transaction devices can ensure proper authentication as well as to unlock specific services. For example, a partition that encodes a specific genetic mutation might be required to access treatment data (e.g., evidence, studies, drugs, patient or population records, etc.) associated with ailments arising from the mutation. The partition may be used as a query to the cOS, which responds by automatically curating healthcare information for consumption by one or more stakeholders (e.g., patient, doctor, insurance provider, technician, etc.).

Figure 3:
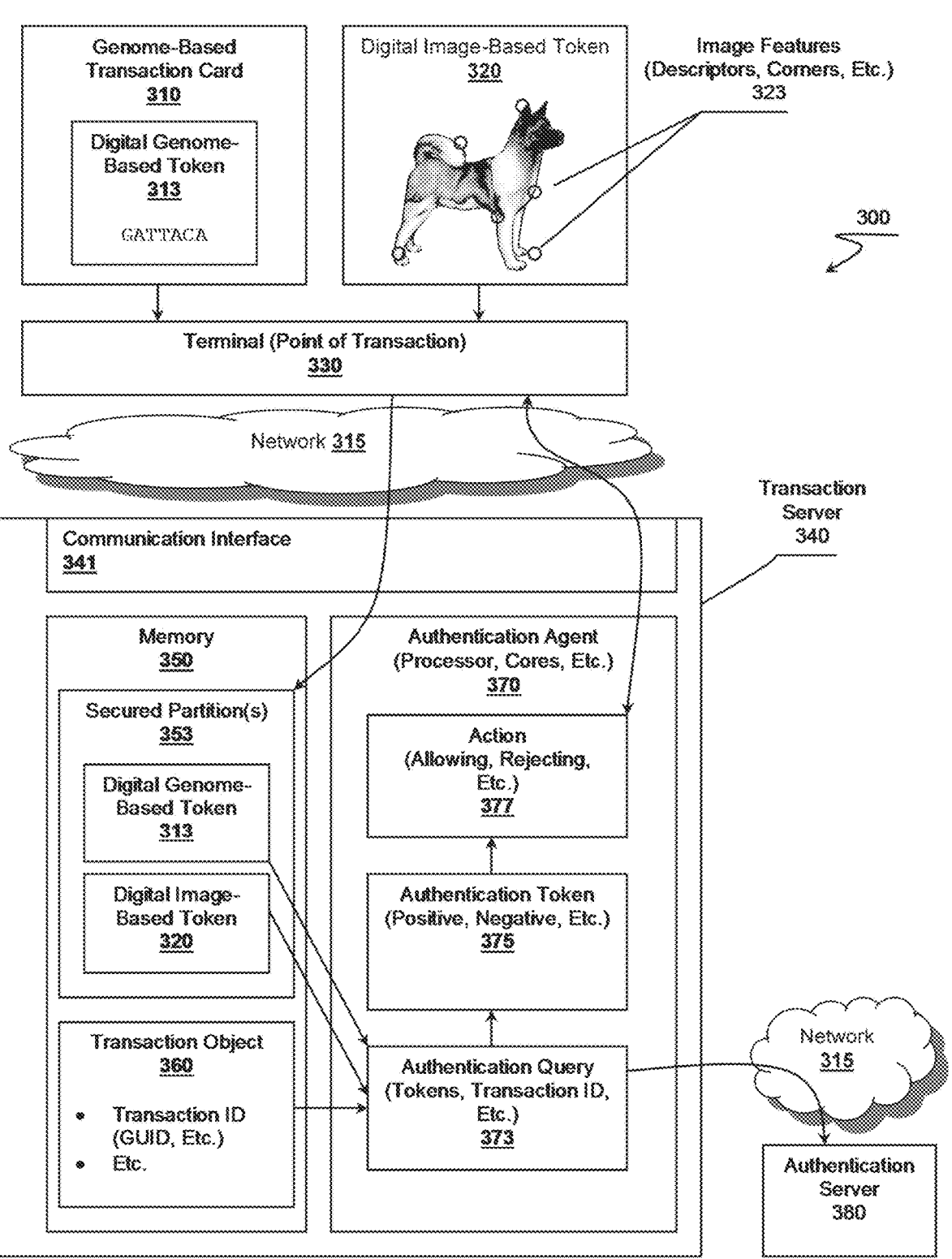
FIG. 3 illustrates a block diagram of an exemplary distributed computer system including an exemplary transaction server that can implement one or more aspects of a genomic data-based transaction system or method according to an embodiment of the present invention.

FIG. 3 illustrates genome-based transaction ecosystem 300 where a possible transaction server leverages information from transaction device 110 in FIG. 1 along with additional personalized information, an image token, as a secondary key that provides additional security. In the example shown, an individual seeks to initiate a transaction represented by transaction object 360 based on at least two pieces of information; digital genome-based token 313 from genome-based transaction card 310 (e.g., a transaction device in a credit card form factor) and digital image-based token 320. Digital genome-based token 313 represents one or more pieces of information related to the genome stored genome-based transaction card 310 and can comprise digital representations of one or more of the following: a genome sequence, a whole genome, a set of SNPs, a set of STRs, a non-sequential string, a DNA string, an RNA string, a hash of genome information, or other genomic data. Digital image-based token 320 represents a personalized, possibly secret, image that both the individual and backend authentication server knows.

Digital image-based token 320 can comprise digital image data representing video data, a video frame, a still image, at least one local image descriptor, a global image descriptor, at least one image feature, or other data constructs derivable from image data. For example, digital image-based token 320 may include a still image of the individual's dog in a particular pose. Alternatively, digital image-based token 320 might include only image features 323 that have been derived from the image. More specifically, image features 323 may comprise SIFT descriptors generated from an implementation of a SIFT algorithm executed on an image of the dog (see U.S. Pat. No. 6,711,293 to Lowe titled "Method and apparatus for identifying scale invariant features in an image and use of same for locating an object in an image", filed Mar. 6, 2000). The types of image features 323 may also include features generated from one or more implementations of the following algorithms: BRISK, SURF, FAST, BRIEF, Harris Corners, Edges, DAISY, GLOH, HOG, EOG, TILT, global descriptors, VLAD, blob descriptors, or other implementations of image analysis algorithms.

It should be appreciated that digital image-based token 320 can be synchronized with valid image-based token objects located on authentication server 380 that have been paired or linked to corresponding genome-based token objects. Thus, digital image-based token 320 may be changed, updated, or modified as desired to provide additional layers of security. For example, an individual may submit a new image or descriptors periodically to authentication server 380 where the new image represents a key required for valid authentication. It should be further appreciated that image-based token objects should be properly bound or linked to corresponding genome-based token objects in order of authentication server 380 to validate an authentication request. In some embodiments, the image features may be encoded as a difference in the consumer's genomic information stored on card 310. For example, a 128 byte SIFT descriptor may be stored as 512 base pairs where each set of four base pairs can store a value from 0 to 255 with a suitable base-four encoding (e.g. AAAA=0, AAAT=1, AAAC=2, AAAG=3, AATA=4, . . . GGGG=255). Image features 323 may be compared to those stored in the genomic information according to a nearest neighbor search. Validity of image features 323 can then be measured based on a distance (e.g., Euclidean distance, Hamming distance, etc.) between image features 323 and those in the genomic information. If the distance is small (i.e., within a threshold 95% confidence level), then the confidence is high that the images features 323 are valid features.

In the example shown, an individual seeks to initiate a transaction, a purchase for example, at terminal 330 representing the point of transaction. Terminal 330 may include a point of sales terminal (e.g., card reader, kiosk, cash register), a mobile device (e.g., cell phone, smart phone, phablet, etc.), a secured genome transaction device, a browser-enabled computer or other device. In this case, the individual allows terminal 330 to obtain digital genome-based token 313 (e.g., digital transaction token 160 in FIG. 1, etc.), perhaps via a card reader or NFC. As a specific example, terminal 330 can include a complementary communication interface to that employed by genome-based transaction card 310, such as the wireless chip system describe described in U.S. Pat. No. 8,554,136 to McCormack titled "Tightly-Coupled Near-Field Communication-Link Connector-Replacement Chips", filed Dec. 21, 2009; U.S. Pat. Nos. 8,714,459 and 8,757,501 to both to McCormack et al. and titled "Scalable High-Bandwidth Connectivity" filed May 14, 2012 and Mar. 4, 2013 respectively; U.S. Pat. No. 8,811,526 to McCormack et al. titled "Delta Modulated Low Power EHF Communication Link", filed May 31, 2012; and U.S. patent application publication 2014/0273856 to Kyles et al. titled "Extremely High Frequency Systems and Methods of Operating the Same", Mar. 13, 2014.

The individual also allows terminal 330 to acquire digital image-based token 320. In some scenarios, the individual may present an image displayed on a screen of their smart phone to a camera on terminal 330. In other cases, the individual can transmit image data (e.g., still image, video, captured image of an object, etc.) to terminal 330 through other types of connections including NFC, 802.11, Bluetooth, WUSB, or other communication techniques. Terminal 330 provides the tokens to transaction server 230 via network 115 (e.g., Internet, PSTN, intranet, LAN, WAN, VPN, etc.).

Transaction server 340 has the responsibility of initiating a transaction should the tokens prove valid as determined by authentication server 380. Transaction server 340 includes communication interface 341, memory 350, and authentication agent 370 executing on one or more processors (e.g., Intel Xeon, AMD Opteron, etc.) within transaction server 340. Communication interface 341 is preferably configured or programmed to communicatively couple with one or more external computing devices over network 115. For example, communication interface 341 can include a communication stack capable of exchange credit card processing protocol packets over a PSTN. Alternatively, communication interface 341 may include a wired, Ethernet or ATM, connection that allows for exchanging data based one on more Internet protocols, possibly secured protocols (e.g., HTTPS, SSL, PKI, etc.).

Memory 350 comprises one or more persistent, non-transitory digital data storage devices (e.g., RAM, Flash, HDD, SSD, etc.) and is configured or programmed to store software instructions associated with authentication agent 370 (e.g., library, program, modules, etc.) and to store other data. In the example shown, memory 350 also stores digital genome-based token 313, digital image-based token 320, and one or more of transaction object 360. In some embodiments, memory 350 can be segmented or partitioned into secured partitions 353 where each of secured partition 353 can be isolated from others and can be assigned to each transaction that is being processed. Isolated partitions can be isolated at a group level, isolated for a specific instance of authentication agent 370, or even isolated for a specific transaction (e.g., transaction object 360). Depending on the desired level of security, secured partitions 353 may also comprise an encrypted partition. As an example, consider a scenario where a doctor wishes to obtain heath or medical records of a patient. An electronic medical records (EMR) server operating as transaction server 340 can establish an encrypted container as part of a doctor-patient session in memory 350 through which tokens and data can be exchanged or stored while ensuring that all data remains confidential.

Authentication agent 370 has numerous roles or responsibilities with respect to initiating a desired transaction. Authentication agent 370 is configured or programmed to receive digital genome-based token 313 and digital image-based token via communication interface 341 from an external device; terminal 330 in this example. In some embodiments, the two tokens may be transmitted without encryption. However, in more secure embodiments, the two tokens are transmitted in an encrypted format (e.g., SSL, 3DES, AES, etc.).

Although the two tokens are illustrated as being distinct, it should be appreciated that the data may be packaged in different ways. For example, both tokens may be combined together as a single token. Consider a case where the individual has selected a picture of their dog as digital image-based token 320. The individual's mobile phone may modify the picture of the dog by integrating or modifying image elements (e.g., gradients, colors, etc.) that would give rise to one or more descriptors as image features 323 as a function digital genome-based token 313. Thus, authentication agent 370 would receive a single image file, or perhaps a single XML stream of descriptors derived from the modified image. Authentication agent 370 is further configured or programmed to store the tokens in memory 350 for further processing. As illustrated, authentication agent 370 may store both the digital genome-based token 313 and digital image-based token 320 within secured partition 353.

Authentication agent 370 is further configured or programmed to link the tokens to one or more of transaction object 360 relating to a transaction associated with an external device. Transaction object 360 represents a data construct that embodies the transaction being processed. For example, transaction object 360 can comprise a transaction identifier that can be used by the various computing devices in ecosystem 300 to determine which transaction is of interest. In view that ecosystem 300 may be quite large or comprise distributed agents across multiple computing devices (e.g., cloud, etc.), the transaction identifier can comprise a unique identifier (e.g., GUID, UUID, etc.). It should be appreciated that the transaction identifier may map or link to one or more of partition identifiers 255 from FIG. 2. Example transactions may include a purchase, a financial transaction, a healthcare transaction, a game transaction, an authentication request, a web service access, a license manager authentication, an authorization request, a protocol transaction, an account transaction, or other type of transaction.

Authentication agent 370 is further configured or programmed to generate authentication query 373 as a function of the at least digital genome-based token 313 and digital image-based token 320. For example, authentication query 373 might include both tokens, one of the tokens, or possibly a hash of the tokens. Authentication query 373 represents sufficient data for authentication server 380 to determine if the combined tokens indeed represent a valid set or pair of tokens with respect to authenticating the transaction being processed. Authentication query 373 further represents a request submitted to authentication server 380, possibly over a secure channel (e.g., SSL, HTTPS, secure electronic transaction, etc.). For example, authentication agent 370 can establish an HTTPS connection over communication interface 341 with authentication server where the data exchanged is encrypted with AES. Authentication query 373 can comprise an XML or JSON stream transmitted to authentication server 380 and that packages digital genome-based token 313, digital image-based token 320, or even the transaction identifier associated with transaction object 360.

Authentication agent 370 is further configured or programmed to receive authentication token 375 related to transaction object 360 from authentication server 380. Authentication token 375 represents the determination by authentication server 380 whether or not the token set or pair comprises valid authentication information. Thus, authentication token 375 can comprise various authentication information including a positive authentication, a negative authentication, an permitted access level, or even an authentication confidences score indicating a certainty with which the token set are considered a valid set.

Depending on the nature of authentication query 373, authentication token 375 may vary. For example, in embodiments where authentication query 373 comprises both tokens and a transaction ID, authentication token 375 might only include the transaction ID, which allows authentication agent 370 to asynchronously track multiple transaction, and an data value indicating if the authentication was positive (e.g., valid) or negative (e.g., invalid), allowing authentication agent 270 to continue forward with processing the transaction. Still, if authentication query 373 includes digital genome-based token 313 but not digital image-based token 320, authentication token 375 might include a corresponding image-based token object. If authentication agent determines the image-based token object is a match for digital image-based token 320, then the transaction can proceed. The reciprocal is also possible where authentication query

373 comprises digital image-based token 320 but not digital genome-based token 313, then authentication token 375 might include a genome-based token object. Again, if authentication agent 370 determines a match between the genome-based token object and digital genome-based token 313, the transaction can proceed.

Authentication agent 370 is further configured or programmed to initiate an action associated with the transaction according to information within authentication token 375. Example actions that can be initiated include allowing the transaction to proceed, rejecting the transaction, requesting additional information for the transaction, chaining transactions, reporting the transaction status, calling APIs or web services, launching software applications or functions, generating alerts or notifications, or other type of transaction.

It should be appreciated that many of the features disclosed in FIG. 3 can be distributed among genome-based transaction card 310, transaction server 340, and authentication server 380. Such an approach increases the secure nature of ecosystem 300 while reducing the risk of a data breach. In the disclosed approach, for example, if the transaction server 340 operating in a retail chain environment (e.g., Target®, Home Depot®, etc.) is compromised, the retailers would not have a permanent record of the tokens, which would expose private information. Although authentication server 380 is illustrated as a distinct server, it should be appreciated that its services may also be integrated into transaction server 340. However, in some embodiments it may be desirable to delocalize one or more features.

Figure 4:
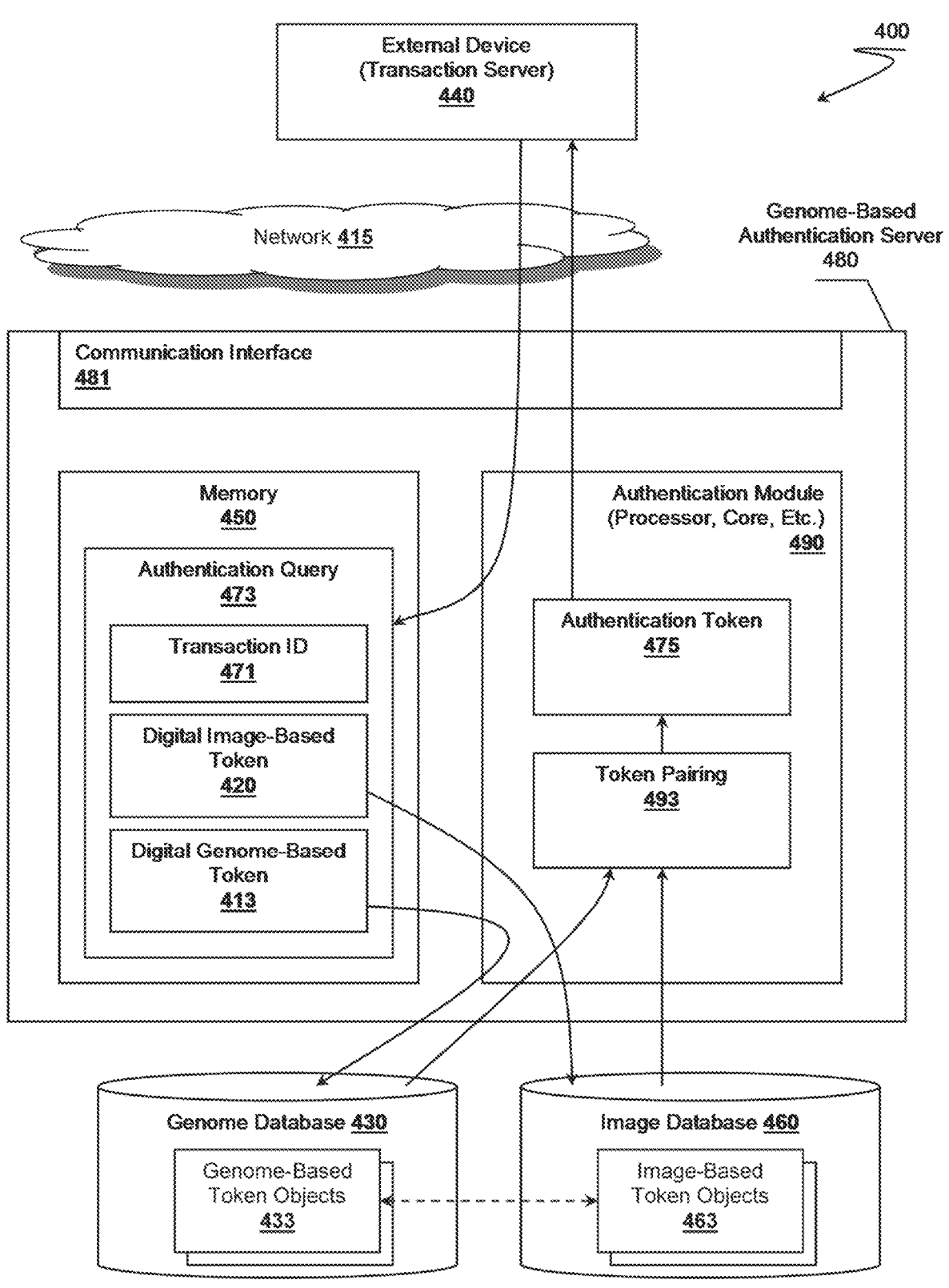
FIG. 4 illustrates a block diagram of an exemplary distributed computer system including an exemplary authentication server that can implement one or more aspects of a genomic data-based transaction system or method according to an embodiment of the present invention.

FIG. 4 illustrates additional details regarding the features of a back-end genome-based authentication server 480 within genome-based authentication server system 400. In the example shown, external device 440, which may be transaction server 340 from FIG. 3, is requesting authentication from authentication server 480 based on authentication query 473 submitted over network 415. Genome-based authentication server system 400 includes authentication server 480, genome database 430, and image database 460.

Genome database 430 is configured or programmed to store genome-based token objects 433. Genome-based token objects 433 represent known genomic information to be used as keys and can correspond to partitions 237 in FIG. 2. Genome-based token objects 433 can comprise a genome sequence, a whole genome, a set of SNPs, a set of STRs, a non-sequential string, a DNA string, an RNA string, or other genomic information. For example, genome-based token objects 433 can be stored as a whole genome in a BAMBAM format as described in U.S. patent application publications 2012/0059670 and 2012/0066001 both to Sanborn et al. and titled "BAMBAM: Parallel Comparative Analysis of High-Throughput Sequencing Data". Each of genome-based token objects 433 can then include locations, lengths, differences, or other information in reference to the whole genome.

In view that genome database 430 can store thousands or millions of tokens for many different individuals, genome database 430 is preferably configured or programmed to store whole genome information for many, many individuals. The whole genome information may be stored in raw formats, e.g., 3 GB per individual or possibly 150 GB per individual assuming 50× reads. In such cases, genome database 430 may require many exabytes of storage, possibly arranged in a RAID system. However, it is also possible that the storage system includes a reference whole genome and each individual's whole genome may only include differences from the reference whole genome to reduce overall storage requirements.

Genome-based token objects 433 can also be linked or point to corresponding image-based token objects 463. The pair of corresponding tokens represents a valid authentication pair where both tokens must have an established correspondence in order for authentication to be considered valid.

Image database 460 is configured or programmed to store image-based token objects 463. Image based-token objects 463 can include video data, a video frame, a still image, at least one local image descriptor, a global image descriptor, at least one image feature, or other derivable property of the image. For example, image-based token objects 463 may include a set of SIFT descriptors or even a global image descriptor corresponding to a personalized image associated with the individual. Each of image-based token objects 463 can also be linked to corresponding genome-based token objects 433 representing a currently valid authentication pair as represented by the dashed line between image-based token objects 463 and genome-based token objects 433.

In some embodiments, the tokens can be linked or bound to each other through including references to the other token's object identifier (e.g., GUID, index, UUID, etc.). This approach allows authentication server 480 to use one type of token to look-up the corresponding companion token. In other embodiments, tokens can be stored according to an addressing or indexing scheme determined by the nature of the companion token. For example, genome-based token objects 433 can be stored or indexed according to image descriptors, perhaps in a kd-tree or spill-tree structure via which a nearest neighbor search can be conducted. Further image-based token objects 463 can be stored or indexed according to genetic sequence strings or partition identifiers 255 as illustrated in FIG. 2.

It should be appreciated that the linking of genome-based token objects 433 to image-based token objects 463 are not required to be static links. Rather, the links can be quite dynamic and change or rotate with time. For example, an individual may submit a new image every day to authentication server 480 through a user interface (not shown). The new image can be analyzed by authentication server 480 to derive new features that are to be linked with one or more genome-based token objects 433. Alternatively, authentication server 480 may inform the individual's transaction device of which picture should be considered active for the day or current authentication period (e.g., minutes, hour, day, weeks, etc.). Perhaps the authentication server 480 identifies personal pictures from a compilation of images from the individual or a social networking site. Still further, authentication server 480 may require the user to capture a picture of a specific object among multiple known personal objects according to a specific pose or juxtaposed relative to other items; perhaps based on the techniques disclosed in international patent application publication WO 2013/126221 to Soon-Shiong titled "Content Activation via Interaction-Based Authentication, Systems and Methods", filed Feb. 8, 2013. Thus, it is possible the links between pairs of tokens may change or rotate periodically.

Consider a scenario where a patient wishes to interact with an electronic medical record exchange to update or to access their medical records. Authentication server 480 may provide a set of personalized images, e.g., 50 images, as image-based token objects 463. The set of personalized images can be rotated throughout the day or other time period where an active image represents the sole valid digital image-based token that can be used for authentication. Similarly, authentication server 480 may also provide a set of BAM or BAMBAM files that are linked to the set of personalized images. This set of BAM or BAMBAM files may also be rotated throughout the day or other time period. Thus, at any given time or based on other contextual trigger (e.g., location, geo-fence, circumstance, time, etc.) there would be only one valid pair of tokens.

Authentication server 480 determines if an authentication request should be validated or invalidated. Authentication server 480 includes communication interface 481, memory 450, and authentication module 490 configured or programmed to execute on at least one processor of authentication server 480. Authentication module 490 configures authentication server 480 to receive authentication query 473 from one or more of external device 440 via communication interface 481 where, for example, authentication query 473 can correspond to authentication query 373 in FIG. 3. In response to authentication query 473, authentication module 490 generates authentication token 475, which provides authoritative information with respect to the authentication request.

Authentication module 490 is configured or programmed to receive authentication query 473 from external device 440 via communication interface 481. Authentication query 473 is stored in memory 450 for processing as shown, e.g., in an isolated partition of memory 450 or other protected area to enforce confidentiality. Authentication query 473 can include multiple data objects representing the authentication request including transaction ID 471, and at least one of digital image-based token 420 and digital genome-based token 413. It should be appreciated that authentication query 473 is just as varied as authentication query 373 discussed with respect to FIG. 3.

In some embodiments, the communication or processing session among the various devices (e.g., genome-transaction device, external device 440, authentication server 480, etc.) can exist within a homomorphic encryption space or a somewhat homomorphic encryption (SHE) space, possibly keyed based on one or more of digital image-based token 420, digital genome-based token 413, genome-based token objects 433, image-based token object 463, transaction ID 471, stakeholder information, or other factors. The homomorphic space allows for transmission of encrypted data and the processing of the encrypted data within the corresponding encryption space without requiring decryption of the encrypted. This approach is considered advantageous because it allows for processing of the secure data without compromising confidentiality or data integrity.

Authentication module 490 is also configured or programmed to establish token pairing 493 associated with at least one of digital image-based token 420 and digital genome-based token 413 based on corresponding linked image-based token objects 463 and genome-based token objects 433. Token pairing 493 comprises a data construct that indicates if a pair of tokens is considered to be a valid or an invalid authentication pair. Thus, token pairing 493 can comprise a valid set of linked image-based token objects 463 and genome-based token objects 433, or an invalid set of image-based token objects 463 and genome-based token objects 433. Authentication module 490 is further configured or programmed to instantiate authentication token 475 as a function of token pairing 493, which is transmitted back to external device 440 via communication interface 481.

It should be appreciated that the digital tokens in authentication query 473 and token objects in the databases can be the same type of data objects. For example, digital image-based token 420 and image-based token objects 463 may both comprise video data, a video frame, a still image, at least one local image descriptor, a global image descriptor, at least one image feature, or other image-related data constructs. Additionally, digital genome-based token 413 and genome-based token objects 433 may both comprise a genome sequence, a whole genome, a set of SNPs, a set of STRs, a non-sequential string, a DNA string, an RNA string, or other genome partition information. For the sake of clarity, the two types of data objects are given different names to aid in describing the data flow.

Although the tokens and token objects may be the same type of objects, it is also possible they may be different. For example, digital image-based token 420 might include a digital image while the corresponding image-based token objects 463 may comprise a set of SIFT descriptors. Authentication module 490 can execute an implementation of a SIFT algorithm on the digital image to derive a candidate set of SIFT descriptors, which are then compared to those in the image database 460. Further, digital genome-based token 413 may comprise a hash value of a genome sequence (see partition 237 from FIG. 2) while genome-based token objects 433 may comprise actual sequences stored in the hash table. Thus, it is possible, in some embodiments, for the tokens and token objects to be near matches rather than exact matches while still representing valid authentication credentials.

There are multiple scenarios by which token pairing 493 can be established. In one embodiment, authentication query 473 might include digital image-based token 420 and lack digital genome-based token 413. In such a case, authentication module 490 can use digital image-based token 420 to query image database 460 to find the corresponding image-based token object 463, if it exists. If it does exist, authentication module 490 can follow the link from image-based token object 463 to determine if there is a currently valid linked genome-based token object 433. Thus, token pairing 493 may include the valid token object pair. In such a case, authentication module 490 instantiates authentication token 475 from token pairing 493 so that authentication token 475 includes the corresponding genome-based token objects 433. External device 440 can compare the corresponding genome-based token object 433 to local digital genome-based token 413 to conduct final authentication analysis. If no valid link exists, token pairing 493 might only include the image-based token object 463 and NULL value for the corresponding genome-based token object 433. In such a case, authentication token 475 might simply include a negative or failed authentication indication to inform external device 440 that the authentication has or would have failed.

Alternatively, authentication query 473 might include digital genome-based token 413 while lacking digital image-based token 420. Similar to above the, authentication module 490 can look up image-based token object 463 that would or should correspond to digital genome-based token 413 via consulting genome database 430 and following links among existing objects. Assuming a corresponding image-based token object 463 is found, then token pairing 493 would reflect the linked token objects. Further, authentication module 490 can instantiate authentication token 475 so that it includes the corresponding image-based token object 463. Again, external device 440 can finalize authentication based on the received authentication token 475 based on its locally stored information.

In embodiments where both tokens are included in authentication query 473 as illustrated, token pairing 493 might include a valid pair of token objects from the database or might include an invalid pair depending on if the database validates that digital image-based token 420 and digital genome-based token 413 are indeed a currently active, valid pair. Thus, authentication token 475 can be instantiated as a function of token pairing 493 and comprise a value indicating a positive authentication (i.e., successful authentication), a negative authentication (i.e., a failed authentication), an access level, an authentication confidence score, or other parameters associated with the attempted authentication. In embodiments having access privileges (e.g., public, protected, private, confidential, secret, top secret, compartmentalized, etc.), the access level information can indicate the maximum level of access permitted based on the credentials in authentication query 473. Further, in scenarios where nearest neighbor information is leveraged (e.g., descriptors stored in trees, kNN searches, etc.) to identify matches between tokens 420 and 413 and corresponding token objects 463 and 433, authentication token 475 can include a confidence score indicating the level of match (e.g., measured distance between tokens and objects within a data representation space, similarity measures, etc.).

It should be appreciated that disclosed authentication server 480 can represent a back end authentication infrastructure. Therefore, authentication server 480 can be configured or programmed to process large numbers of authentication query 473 substantially in parallel. For example, a server system having a server equipped with an Intel Xeon 8-core processor may generate at least 100 authentication tokens per second, more preferably at least 1,000 authentication tokens per second, and yet more preferably at least 10,000 authentication tokens per second.

Figure 5:
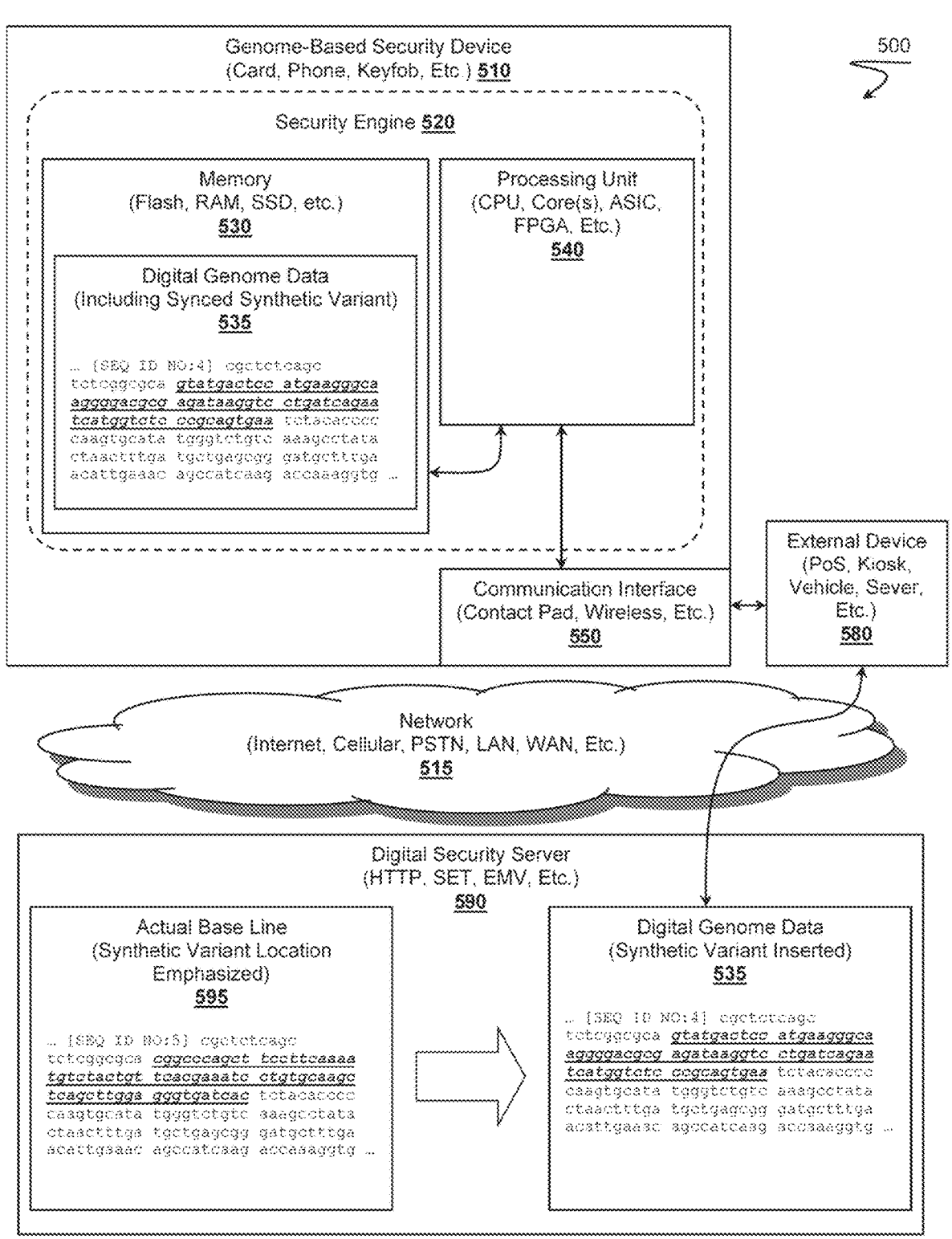
FIG. 5 illustrates a block diagram of an exemplary distributed computer system including an exemplary genomic synthetic variant-based security device that stores digital genome data 535 marked as SEQ ID NO: 4, and an exemplary genomic synthetic variant-based digital security server that stores actual base line 595 marked as SEQ. ID NO: 5 that may be compared to digital genome data 535 marked as SEQ ID. NO: 4, and that can implement one or more aspects of a genomic data-based transaction system or method according to an embodiment of the present invention.

FIG. 5 illustrates a networked environment, referred to herein as ecosystem system 500 where genome-based security device 510 can cause a transaction among multiple devices (e.g., security device 510, external device 580, remote digital security server 590, etc.) through leveraging digital genome data 535 for authentication or authorization of the transaction. Genome-based security device 510 includes memory 530, processing unit 540, and communication interface 550, through which genome-based security device 510 is able to communicatively couple with external device 580. For the sake of discussion, genome-based security device 510 will be described with respect to a credit card form factor. However, it should be appreciated that other form factors are also contemplated. For example, security device 510 may be embodied as a cell phone, tablet, keyfob, gaming device, cash register, vehicle, or other type of computer-based device.

Processing unit 540 includes one or more computer microprocessors configured to execute software instructions stored in memory 530. Examples of suitable processors include M.O.S.T. Card® C-Series, Intel® single or multi core processors, AMD® processors, ARM-based processors, Freescale® processors, or other appropriate processors. The selection of a processor also depends on the form factor of security device 510. A small, thin device having a credit card form factor would be best served by a thin, low powered chip. A larger device having cell phone form factor would likely be best served by a multi-core ARM processor. An intermediary device possibly having the form factor of a smart watch may leverage an ARM Cortex-M4 processor. Power may be supplied via a rechargeable battery; a Li-Polymer batter for example.

Communication interface 550 can take on various forms depending on the desired nature of genome-based security device 510. In embodiments where security device 510 comprises a credit card or smart card form factor, communication interface 550 may comprise a contact pad. The contact pad can be constructed to adhere to one or more standards as well as support one or more financial communication protocols (e.g., SET, EMV, etc.). In other more interesting embodiments, communication interface 550 comprises a wireless interface. For example, communication interface 550, in some embodiments, includes a 60 GHz chip set capable of exchanging data with a similarly enabled external device 580. One possible 60 GHz chip set includes those provided by Keyssa, Inc. (see URL keyssa.com). The Keyssa technology provides several advantages. First, the technology has low power requirements, which can be met by a rechargeable battery. Second, the chip set comprises a short range less than 10 cm (e.g., about 1 cm), which prevents others from sniffing the wireless exchange as can happen with WiFi or other longer range wireless technologies. Third, the chip set supports high speed communications on the order of 6 Gbps. Such speeds enable exchange of vast quantities of digital data quickly; 750 MB of genomic data may be transferred within one second for example. Thus, a user may authenticate a transaction based on an exchange of the synthetic variant information with minimal observed latency by the user. Still, other acceptable wireless interfaces may include WiFi, WiGIG, Bluetooth, Wireless USB, RF, or other technologies.

Memory 530 represents non-transitory computer readable media that can persistently store digital data. Memory 530 can include one or more suitable memory storage devices possibly comprising RAM, flash, solid state drives, hard disk drives, or other type of digital storage. In embodiments, having a thin form factor, a credit card form factor for example, memory 530 would likely be flash memory. In larger devices, memory 530 may include a solid state disk or even a low powered hard disk where the drives are configured to support one or more file systems. In some embodiments, portions of memory 530 that store sensitive information such as digital genome data 535 and/or associated synthetic variants can be secured. For example, a portion of memory 530, perhaps as a separate chip, can be configured to adhere to a desirable level of the FIPS 140 standard (see URL csrc.nist.gov/groups/STM/cmvp/standards.html). In addition to or alternatively, the portion of memory 530 storing the synthetic variant can be encrypted as a secured container, possibly based on the VeraCrypt (see URL veracrypt.codeplex.com) or similar technology.

Memory 530 is configured to store digital genomic data 535 that is associated with at least one biological entity. The biological entity, in most embodiments, will be a human being. However, it is also contemplated that the biological entity may include other animals, possibly including prized livestock, thoroughbreds, pets, or other entities. In some embodiments, digital genomic data 535 may represent genome information associated with a larger cohort beyond a person. For example, the genomic data might generally be common among a family, community, ethnicity, species, genus, tissue types, tumor types, or other cohort. The remaining portions of the discussion will present the inventive subject matter from the perspective that the digital genome data 535 is associated with a unique human being.

Digital genome data 535 comprises digital data representative of a person's genome. In some embodiments, digital genome data 535 can comprise significant portions of the person's whole genome sequence (WGS), which may represent many gigabytes of data depending on the format and quality of the sequence. In more compact embodiments, digital genome data 535 may represent just a portion of the person's WGS. For example, digital genome data 535 might only comprise the person's exome or a portion of the exome; possibly about 1% to 2% of the WGS. Such embodiments would reduce the memory footprint of digital genome data

535. It should be appreciated that digital genome data 535 may take on other forms beyond a DNA representation. In other embodiments, digital genome data 535 might include RNA, mRNA, tRNA, gRNA, proteomic data, or other types of data. Further, it should be appreciated that digital genome data 535 may comprise metadata beyond a raw sequence. Example metadata may include sequence machine reads, quality scores, location information, time stamps, or other information that describes the nature of digital genome data 535.

Of particular interest, digital genome data 535 includes a synthetic variant as represented by the highlighted portion of digital genome data 535. The synthetic variant represents a portion of the genome data that is different from the person's actual genomic information. The difference represented by the synthetic variant can be considered a security feature that prevents external threats from discovering a person's genome and then stealing the person's identity. Even if the threat is able to steal a tissue sample from the person, the threat would be unable to determine (without great effort) or discover the synthetic variant "secret".

It should be appreciated that remote digital security server 590 can operate as authorization or authentication agent based on the synthetic variant. In the example shown, digital security server 590 stores the person's genomic actual base line 595. The highlighted portion of actual base line 595 represents a section of the person's genome where the synthetic variant should be placed as indicated by the highlighted portion of digital genome data 535 located on both digital security server 590 and memory 530. Thus, the person's WGS cannot be compromised by a threat (e.g., a malicious person or entity) stealing the card. The distribution of the WGS information and synthetic variant provides at least two advantages. First, as just mentioned, the WGS data is stored on the remote security server rather than genome security device 510 so that if security device 510 is lost or stolen, the person's complete genome is not compromised. Second, the synthetic variant ensures that a threat cannot (without access to device 510) leverage the person's genomic data to conduct illicit transactions.

Although the synthetic variant is presented by a genome sequence of 70 base pairs, it should be appreciated the synthetic variant can take on a broad spectrum of attributes. The length of synthetic variant may extend from a single base pair; to at least 100 base pairs; to 10,000 base pairs; to more than 1,000,000 base pairs; or even more than 10,000,000 base pairs. The length or size of the synthetic variant is not considered a problem with respect to data exchanges. Consider where each base pair is represented by binary packed data using the bit patterns {A:00, C:01, G:10, T:11} as a very simple example. A synthetic variant having 10,000,000 base pairs may be encoded in 20,000,000 bits, or about 2,500,000 bytes. Such a compact representation would easily fit within memory 530, along with other genomic data 535. Further, transferring the 2.5 MB synthetic variant over a 60 GHz, 6 Gbps wireless interface would take about 0.003 seconds. Therefore, using such large synthetic variants as keys, tokens, or secrets, does not present a problem from a communication latency perspective.

In view that the synthetic variant can be of any length, it should be appreciated that one or more synthetic variants can be instantiated to have sufficient length or structure to match a target security need. Longer lengths or more complex structures can serve for transactions requiring additional security (e.g., healthcare transactions, major financial transactions, etc.). Shorter lengths or less complex structures may serve for less critical needs (e.g., small commercial transactions or payments, quick identity checks, etc.).

With respect to structure, the synthetic variant can also comprises a wide variety of structures. In some embodiments, as shown, the synthetic variant may include one or more contiguous sequences. Still, in other embodiments, the synthetic variant may comprise non-contiguous base pairs. For example, the synthetic variant might include 10,000,000 altered non-neighboring base pairs spread across the WGS, the exome, a chromosome, or other aspect of the genomic data. In such a case, the synthetic variant would include alterations that appear like a single nucleotide polymorphism (SNP) or a large set of SNPs distributed across the genome.

In some embodiments, the synthetic variant can be constructed or instantiated to respect the nature of the replaced section of actual base line 595. Consider as an example a scenario where the synthetic variant is associated with a specific gene in a person's exome. Before replacement, the Shannon entropy of the gene may be calculated. Then, security server 590 or other management device can construct the synthetic variant so that it would maintain or conserve the calculated Shannon Entropy of the gene. Such an approach is considered advantageous because it reduces the risk of a threat detecting which portions of digital genome data is artificial. Other attributes of actual base line 595 that may be conserved, at least to within threshold values, include length, nucleotide count (i.e., number of A's, T's, C's, and G's), number or types of codons, or other properties. In embodiments were the synthetic variant is intended to be stored according to standardized format (e.g., SAM, BAM, GAR, etc.), example conserved metrics also include average depth of coverage, machine error rates, or other factors.

The synthetic variant can also be constructed or otherwise instantiated to appear as a specific type of variant with respect to the person's genome so that, when analyzed in aggregate, the synthetic variant appears as a natural feature rather than an artificial construct. For example, the synthetic variant may be constructed to mimic one or more of an insertion, a deletion, a duplication, a rearrangement, an inversion, a translocation, a loss of heterozygosity, or other genomic feature. Such an approach is considered advantageous because it aids in occluding which genomic features in the digital genome data 535 are artificially created. Further, this approach gives rise to additional security features. Rather than merely relying on the sequence of the synthetic variant as a key or token, the juxtaposition of such artificially created features in aggregate can become the key. A more specific example might include instantiation of a set of artificial indels so that a graphical representation of the person's genome presented in a circular graphic orientation yields a specific pattern, which becomes the key.

An especially interesting type of synthetic variant can include differences generated, discovered, or identified by comparing the person's genome with a reference genome and/or other genomes (e.g., tumor tissue, etc.). Such differences can be found or created from use of BAMBAM techniques as described in U.S. patent application publications 2012/0059670, filed May 25, 2011, and 2012/0066001, filed Nov. 18, 2011, both to Sanborn et al. and titled "BAMBAM: Parallel Comparative Analysis of High-Throughput Sequencing Data". Such techniques give rise to identified differences relative to one or more reference genomes where the differences can then be used as synthetic variants to authorize transactions. An astute reader will appreciate that such differences are not required to be relative to or originate from the person. Rather, the difference may originate from other entities. In such cases, the synthetic variant would be naturally occurring, but just not from the person of interest. Thus, an analysis of digital genome data 535 would yield information only indicating the synthetic variant appears as a natural part of the genome data.

It is also possible to encode information within the synthetic variant. When synthetic variant is constructed or otherwise instantiated, a variant generation module (not shown) can create nucleotide sequences to present the desired information perhaps encoded using a base-four format as referenced previously. For example, nucleotide sequences may be used to encode non-genomic information possibly including account numbers, an entity identifier (e.g., SSN, driver's license number, etc.), a stakeholder preference, an access level, a permission, a secret token (e.g., public-private key, etc.), a digital object identifier, a healthcare object identifier, a human object identifier, a uniform resource locator, metadata, or other information. In some embodiments, large amounts of non-genomic information may be stored or otherwise encoded and that represent different types of data modalities. A color 1000×1000 pixel image may be encoded as a bitmap in a synthetic variant having roughly 750,000 base pairs assuming an RGB image and a naïve binary encoding. Thus, the synthetic variant can also encode images, videos, audio files, software instructions, or other features. The advantage of such an approach is clear. Beyond the synthetic variant providing security features, the encoding also provides for a human consumable data construct; a user may validate that the image encoded in the synthetic variant is indeed the correct image, once decoded, for example.

Responsibilities of management or use of the synthetic variant with respect to genome-based security device 510 falls on security engine 520. Security engine 520 represents a combination of software instructions stored in memory 530 and processing unit 540. Security engine 520 is executable on processing unit 540 (e.g., CPU, core, ASIC, etc.) and configures processing unit 540 to execute the roles or responsibilities associated with the synthetic variant. More specifically, security engine 520 maintains synchronization of the synthetic variant with respect to synthetic variant data stored on remote digital security server 590, possibly remotely accessible over network 515 (e.g., Internet, intranet, LAN, PSTN, WAN, cellular, etc.).

It should be noted that the example shown illustrates that the synthetic variant stored in memory 530 is the same as the synthetic variant stored on digital security server 590. Thus, the example illustrates a case where the synthetic variant on genome-based security device 510 is the same as and synchronized with the synthetic variant data of server 590. However, other embodiments are also contemplated. For example, digital security server 590 may store data representing software instructions or other types of data on how to generate the synthetic variant without necessarily being required to store the actual synthetic variant. In such cases, security engine 520 ensures that the synthetic variant stored in memory 530 is synchronized with the synthetic variant data on digital security server 590 so that the synthetic variant corresponds with the data. While the synthetic variant data may indeed include the actual variant, it may also or alternatively include information about how to generate the variant; implementations of algorithms, parameters, timestamps, or other data for example.

Security engine 520 is configured to or programmed to cause external device 580 to participate in one or more transactions. In the example shown, security engine 520 is able to communicatively couple with external device 580 via communication interface 550. For example, security engine 520 can exchange at least the synthetic variant, and possibly other data including portions of digital genome data 535, with external device 580. In some embodiments, external device 580 consults with digital security server 590 to determine if the transaction should proceed as a function of the synthetic variant data and possibly including the digital genome data 535.

As a more specific example, consider a scenario where genome-based security device 510 is embodied as a healthcare card storing a patient's healthcare history as secured by the synthetic variant. Such a card can be equipped with a short range 60 GHz wireless communication interface. When the patient attends an appointment with their healthcare provider, the provider can place the card near the provider's tablet computer having a complementary 60 GHz interface. In this example, the provider's tablet operates as external device 580. The tablet receives the synthetic variant and/or digital genome data 535 (e.g., exome data, WGS data, etc.) possibly via a secure protocol if desired, and then attempts to seek authorization to access the patient's healthcare history on the card. The tablet can use the synthetic variant, along with other security data, to send a request to digital security server 590. If digital security server 590 finds that the request satisfies authorization or authentication requirements, digital security server 590 can respond with an authorization packet, which the tablet can use to gain access to the healthcare history stored in memory 530. In this example, the transaction in which the tablet participates is a healthcare transaction.

Figure 6:
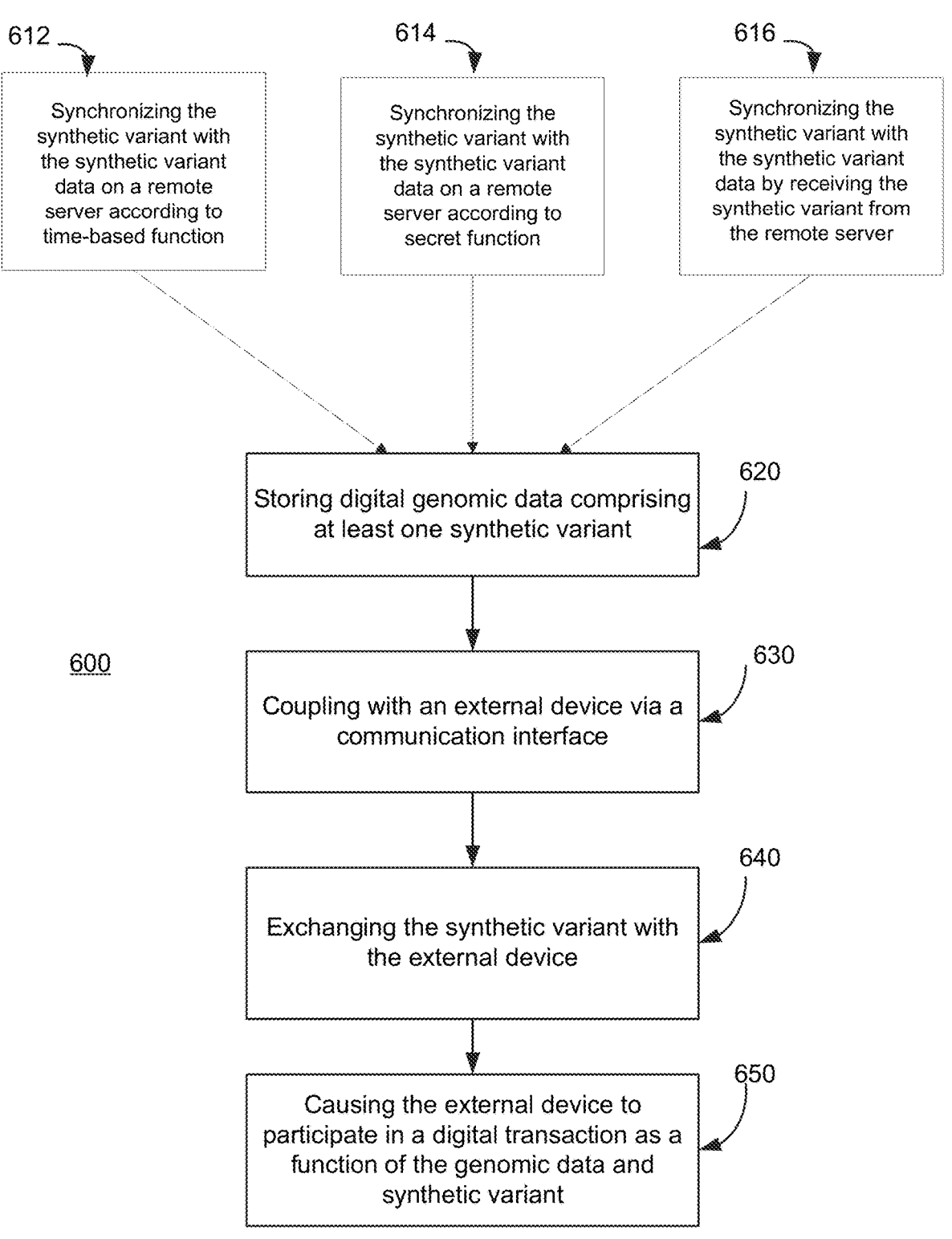
FIG. 6 illustrates an exemplary method for authorizing a secure transaction including synchronization of at least one synthetic genomic variant and digital genomic data in accordance with an embodiment of the present invention.

FIG. 6 provides additional details regarding the roles or responsibilities of security engine 520 in the form of method 600. Method 600 outlines how a security device (e.g., genome-based security device 510) can cause external device 580 to participate in a transaction as a function of the synthetic variant.

Steps 612, 614 and 616 include the security engine maintaining synchronization of the synthetic variant with respect to synthetic variant data stored on a remote digital security server. Maintaining synchronization can be a self-contained process or an interactive process. In some embodiments, the security engine actively manages the synchronization process by directly interacting with the synthetic variant information stored in the local memory. However, in other embodiments, the security engine can take on a more passive role by receiving the synthetic variant, possibly via a secured protocol (e.g., SSL, TLS, SSH, SFTP, IPsec, Kerberos, etc.) from the remote digital security server and then storing the received variant. Still, there are numerous possible techniques by which the security engine can maintain synchronization of the synthetic variant.

One possible approach by which the security engine can maintain synchronization is through a time-based function. Step 612 can include the security engine synchronizing the synthetic variant with the synthetic variant data on the remote security service according to the time-based function. As briefly described previously, the security engine can rotate through or progress through possible synthetic variants using time information (e.g., timestamp, real-time GPS time, etc.) as input to a variant generator.

As another more specific time-based example, consider an embodiment that leverages a cryptographic module (e.g., ASIC, FPGA, STM7007, software library, etc.) as a synthetic variant generator. Such an embodiment may generate a synthetic variant based on repeated application of an implementation of a cryptographic algorithm (e.g., SHA, AES, 3DES, ECC, etc.). The security engine may generate a new synthetic variant based on a timestamp and a previous synthetic variant. Further the security engine maintains synchronization with the remote digital, which in parallel and independently generates the same new synthetic variants according to the same algorithms. For example, at timestamp T1 both systems generate the new synthetic variant (SV1) by passing T1 and the old synthetic variant (SV0) to their respective implementations of the encryption algorithm. The result is then converted to a nucleotide sequence through a conversion process where the digital data results are mapped to the nucleotides. At T2, the process is repeated. The periodicity between the timestamps can be regular (e.g., every five minutes) or irregular as long as the two systems remain in synch with respect to their processes. Such an embodiment can leverage cipher block chaining (CBC) to generate new blocks of data from the algorithms to ensure sufficient data is available to meet length requirements for the synthetic variant. It should be appreciated that other forms of block cipher modes are also considered applicable including PCBC, CFB, OFB, or others.

It should be appreciated that the time-based function can take on different dependencies with respect to time. The time-based function may operate based on an absolute time, a relative time, a periodicity, or other time factors. For example, the synthetic variant might be generated based solely on an initial absolute timestamp (e.g., time of creation, birth date and time, time of transaction, etc.). The time-based function is not required to be dynamic where it continually generates new synthetic variants periodically as in the previous example. Rather, as needed the time-based function that generates a synthetic variant on demand from an absolute time, possibly obtained from the external device or GPS sensor, might be more practical for genome-based security devices that are not self-powered.

Another technique for maintain synchronization of synthetic variant information between the security engine and the remote digital security server is described by step 614. Step 614 can include synchronizing the synthetic variant with the synthetic variant data on the remote digital security server according to a secret function. A secret function represents an implementation of an algorithm that is secured via a "secret" token or key. The key can be combined with other types of data (e.g., old synthetic variants, timestamps, other metadata, etc.) as input into the secret function. For example, a person's password (i.e., a secret token) can be concatenated to or otherwise combined with an old synthetic variant as input. The combined data may be passed to a hash function that generates a new token. The new token may then be used as a key input to an implementation of an AES algorithm that converts the old synthetic variant to cipher text, which is in turn is translated into a new variant, possibly using a suitable binary data to nucleotide base encoding (e.g., 00 to A, 01 to T, etc.). It should be also appreciated that the secret function may also operate as part of a PKI or a public-private key exchange ecosystem.

Still another technique by which the security engine can maintain synchronization with the remote digital security engine is described in step 616. Step 616 comprises the security engine synchronizing the synthetic variant with the synthetic variant data on the remote digital security server by receiving the synthetic variant from the server. In such embodiments, the security engine can simply receive one or more packets of data via the genome-based security device's communication interface, possibly over a network via a secured protocol. Alternatively, the genome-based security device may be provisioned with the synthetic variant, obtained from the server, at the time of manufacture. Still further, in some embodiments, the security engine may, on a periodic basis (e.g., hourly, daily, weekly, every five minutes, etc.) download a new synthetic variant directly from the server via a secured protocol.

Other methods of maintaining synchronization are also possible beyond those listed with respect to steps 612, 614, and 616. Another possible technique that may be employed especially in personal area networks (PANs) includes the genome-based security device communicating with a hub device in the PAN; a person's cell phone, smart watch, or other personal device for example. The cell phone can provide synchronizing services, timestamp services, cryptographic services, or other services to the person's genome-based security device; their electronic healthcare card for example. Such an approach is considered advantageous in embodiments where a wireless carrier may operate as a data record custodian. For example, in some international jurisdictions healthcare is commoditized or follows a retail model, and lacks centralized electronic medical records. In such cases a person might be responsible for their own records, which may be stored on the wireless provider's servers. Thus, the person's cell phone would operate as a central hub for healthcare data. The cell phone may operate as the genome-based security device or may operate as the external device through which a person's electronic healthcare card can maintain synchrony of the synthetic variants stored on the custodian's servers.

Step 620 includes the security engine storing digital genome data comprising at least one synthetic variant in the memory of the genome-based security device. In some embodiments, the digital genome data is populated in the memory at the time of manufacture. In other embodiments, the digital genome data can be stored in the field, possibly at a point-of-service or over a secure network connection. The synthetic variant can be stored along with one or more portions of the digital genomic data at the same time. For example, a remote digital security server may provide a WGS or exomes that comprises the synthetic variant over a secured internet connection as a bulk file. Still, in other embodiments, the synthetic variant may be locally created and stored by the security engine.

Consider a scenario where a user provides a secret key via a back channel (e.g., direct telephone connection, etc.) to the digital security server and to the security engine. Both computing devices may use the secret key to locally generate the synthetic variant using a commonly known function, for example, an implementation of the Scrypt hash algorithm. This approach is considered advantageous because the synthetic variant is not required to be exchanged.

The digital genome data and synthetic variant can be stored according to one or more formats as discussed previously. In some embodiments, the synthetic variant may be stored in a BAM format, SAM format, GAR format, VCF format, or other standardized or proprietary formats. Further, the synthetic variant may be stored as part of a larger file, a BAM file for example, or may even be stored as a standalone variant file.

Step 630 includes the security engine commutatively coupling with an external device via a communication interface. As discussed previously, the security engine, by way of the genome-based security device's processing unit, can couple with the external device via a wired interface, a wireless interface, a contact pad interface, or other type of communication interface. Further, the security engine can be configured or programmed to adhere to a data exchange protocol, possibly based on a PKI protocol before the synthetic variants is actually exchanged as suggested by step 640.

Step 650 comprises the security engine causing the external device to participate in a digital transaction as a function of the digital genomic data, including the synthetic variant. Once the external device is armed with sufficient authorized or validated genomic data, possibly based on an additional exchange with the remote digital security server, the external device can complete or otherwise engage with one or more target transactions.

The type and nature of the transactions can also be quite varied. Example transactions that may leverage the disclosed techniques include protocol transactions, financial transactions, commercial transactions, healthcare transactions, other types of transactions. Protocol transactions can leverage the techniques to enable authentication or authorization of individuals as they access on-line resources; a social network or an on-line account for example. In such cases, the digital genomic data coupled with the synthetic variants can uniquely identify a person with respect to their social network allowing increased confidence that the person is actually behind their postings. The risk of a threat posing as the person is reduced due to the difficulty of the threat being able to crack or discover the synthetic variant.

In a similar vein, financial transactions also would benefit from the use of the synthetic variant approach. Financial transactions, transactions involving financial institutions (e.g., banking, trading, account transfers, etc.) would require stronger security due to the sophistication of potential threats. The disclosed approach provides for establishing arbitrarily long synthetic variants where the length of the variants is considered to increase the strength of the security. In such embodiments, it is possible that the genome-based security device may store multiple synthetic variants of various strengths/lengths for different purposes where longer length variants might be bound to specific financial accounts or types of transactions on a one-to-one basis for example.

Commercial transactions are similar to financial transactions but rather focus on payment or purchase of goods or services. In such cases, the synthetic variant might be unique to the vendor as well as the person wishing to participate. As one example, the synthetic variant may include an account identifier for both the vendor and the person. The account identifier may include a bank account ID, a routing number, a cryptocurrency address (e.g., BitCoin, LiteCoin, PeerCoin, etc), a PayPal® account, or other account information. In such a case, similar to the financial transactions discussed above, the synthetic variant may be considered unique to the vendor-person pair.

One very interesting arena that can leverage many features of the disclosed technology includes the healthcare arena. In the healthcare space, privacy is of great concern as is data ownership and retention. Further, healthcare data can be accessed according to many different permission levels. For example, a patient's gender is not as critical as their prognosis for a terminal disease where each type of data may easily require different authentication or authorization levels before access is granted. In ecosystems that support healthcare transactions via which a patient's healthcare data is exchanged, a genome-based security device operating as patient's healthcare card can store or generate numerous synthetic variants, each with different strengths or security requirements. Low strength variants may grant access to low level data while high strength variants may grant access to records of greater importance.

As a use case in the healthcare space, consider a scenario where a doctor, perhaps an oncologist, has a device (e.g., cell phone, tablet, phablets, etc.) that operates as their data assistant when working with patients. At the beginning of the day, the oncologist may place their device in a docking station or cradle. In some cases the docking station may include a wired interface while in other cases the docking station may leverage a wireless communication interface (e.g., 60 GHz, etc.). Based on the oncologist's synthetic variants stored on the device, the device can authenticate the oncologist and upon receiving proper authorization the device can download all the medical records associated with patients that the oncologist will visit that day. The medical records can be downloaded into secured containers (e.g., virtual machine, Docker, etc.) for each patient. In this specific situation, the doctor's device is the genome-based security device and the docking station or cradle operates as the external device that participates in the healthcare transaction.

When the oncologist meets with the patient, the patient may use an electronic healthcare card to unlock their container on the doctor's device. For example, the card may also have a 60 GHz short range wireless interface that is complementary to the doctor's device. In this scenario, the patient's card operates as the genome-based security device and the oncologist's device operates as the external device. Once the doctor's device receives authorization based on the patient's synthetic variant data from the patient's card, the device can unlock the patient's data for consumption by the stakeholder during the appointment. The patient's data may be unlocked permanently or may be unlocked for a specified amount of time.

A synthetic variant can include metadata beyond the raw nucleotide sequences. Storing synthetic variant metadata provides additional information by which the security engine, or other management modules, manage the synthetic variant as a data construct or data object. The metadata can include code or other software instructions by which the security engine generates new versions of the synthetic variant for example. Other metadata might relate to the nature of the variant and may include a start location, a stop location, a length, or other position related information. Further, the metadata might include a number indicating how many non-contiguous portions compose the variant and their location information. Additional metadata can include data indicating what type of variant that the synthetic variant is intended to mimic: a copy number variant (e.g., gain, loss, etc.), duplication, deletion, insertion, tandem duplication, translocation, chromosomal mutation, breakpoints, complex variants, sequence alteration, or other type of information. Interestingly, in some embodiments, the metadata of the synthetic variant may be encoded directly into the synthetic variant.

As described above, embodiments of the present invention exist within a cOS environment. A cOS can comprise an HPaaS (Health Platform as a Service), deployed over a special-purpose healthcare cloud to enable creation of patient-centric healthcare delivery solutions. The cOS creates a globalized patient-centric representation, and provides a powerful set of RESTful data access and process APIs, to allow collaborative healthcare applications to be built and hosted. As an HPaaS, the cOS simplifies the creation of complex clinical workflow applications. The cloud-based API allows developers to easily create centralized web services or distributed and lightweight mobile applications, which can be authenticated based on the disclosed techniques. The cOS maintains a library of extensible external data representation (XDR)-based connectors. Through the connectors, cOS aggregates and synchronizes distributed and disparate structured and unstructured information from EHR, HIS, and PACS into its globalized patient-centric database. The cOS is designed according to service-oriented architecture (SOA) principles. Its RESTful data access and service interface connects people (e.g., stakeholders, patients, providers, payers, etc), devices, and processes to allow collaborative and interactive services and applications to be developed and hosted. Example cOSes that can leverage the disclosed techniques are described in U.S. Pat. No. 8,689,008 to Rangadass et al. titled "Operating System", filed Aug. 5, 2009; and U.S. patent application publications 2011/0313787 to Rangadass et al. and also titled "Operating System", filed Jun. 16, 2010; U.S. 2013/0054272 to Rangadass et al. titled "System and Method for a Healthcare Monitoring Framework in a Network Environment", filed Oct. 24, 2013; U.S. 2013/0144653 to Rangadass et al. titled "System and Method for Visualizing Patient Treatment History in a Network Environment", filed Jan. 29, 2013; U.S. 2013/0166317 to Beardall et al. titled "System and Method for Visualizing Patient Treatment Measures in a Network Environment", filed Feb. 21, 2013; U.S. 2013/0304512 to Seshadri et al. titled "System and Method for Sharing Data in a Clinical Network Environment", filed Jul. 16, 2013; and U.S. 2013/0304496 to Rangadass et al. titled "System and Method for Optimizing Clinical Flow and Operational Efficiencies in a Network Environment", filed Jul. 16, 2013.

One exemplary use case of embodiments of the present invention is from the perspective of a hospital environment. However, it should be appreciated that the subject matter is applicable to other healthcare environments. In this exemplary use case, a patient has a transaction card having a memory, a communication interface, and a transaction module. The transaction card comprises a credit card form factor with a contact pad interface. Still, other embodiments are also possible. For example, the patient's transaction device may comprise their cell phone. The transaction card may be considered a "Guardian Card" or other type of secure card as discussed in the other related documents. The term "Guardian Card" is used here euphemistically to reference a transaction device regardless of its form factor. In some embodiments, the Guardian Card may represent a virtual or digital construct that can be migrated from one digital device to another possibly embodied as a cOS transaction card agent; perhaps from a first version of a credit card form factor to a new version of the credit card form factor having greater memory capacity and faster processor.

In an exemplary use case, the patient arrives at a hospital, perhaps at an emergency room, and engages with a kiosk operating as a device within the cOS environment. The patient places their Guardian Card near a docking port of the kiosk. The kiosk detects the presence of the card and reads the card, possibly via a NFC or proximate wireless interface as described in the related documents. The kiosk obtains relevant transaction tokens or other information from the card and consults its cOS security databases. Upon authentication or authorization, the kiosk can transmit contextually relevant data (e.g., clinical data, genomic data, medical history data, etc.) to the card.

Other stakeholders in the cOS environment can also participate within the ecosystem. Nurses, clinicians, or other healthcare professionals can be updated with respect to the patient's treatment via the cOS alerting system as soon as the patient engages with the kiosk. Further, the Guardian Card can be further configured to track treatment or even operate as one or more of a debit card, credit card, healthcare spending account (HSA) card, loyalty card, insurance card, ID card, or other type of smart card. As various actions are taken, the Guardian Card's memory can be updated according to the parameters of each type of account. Actions or activities that reflect updates to the card may include numerous types of activities including crediting or debiting accounts, adding or removing digital or crypto currency to the card, adjusting loyalty points, modifying or updating medical histories, updating or modifying genomic information, changing user preferences, clinical studies, or other types of actions.

In another exemplary use case of embodiments of the described invention, a patient is using their transaction Guardian Card to interact within a pharmacy. Although not shown, it should be appreciated that the pharmacy and the hospital in the exemplary use cases described herein can be communicatively coupled with each other via the cOS system. For example, a single patient might interact with both institutions in the same day. The cOS system can establish a homomorphic encryption session among the Guardian Card, the pharmacy, and the hospital to allow all participants to exchange data in a secure, confidential manner without exposing their data to each other.

The patient uses their Guardian Card to check into the pharmacy, possibly via a kiosk or docking stations similar to the exemplary hospital use case described above. Once checked in or otherwise authenticated, the pharmacy may download prescription information (e.g., dosages, drugs, drug-drug interactions, drug-gene interactions, allergies, user preferences, insurance, benefits, etc.) or other information. The communication can be conducted in a secure manner, possibly based on genome-based transaction tokens. Additionally, the pharmacy can also upload information to the Guardian Card possibly including the drug information, manufacturer, pharma studies, or other data.

Upon the patient checking into the cOS system, the cOS alerting system can notify the pharmacist of the patient's presence. Further, the cOS provides the prescription information to the pharmacist, who can then fill the prescription. When the patient obtains their prescription and checks out, again the Guardian Card can be updated so that the data stored in its memory properly reflects the various account information (e.g., secure debit balance, credit card data, loyalty points, health spending account data, etc.).

In yet another exemplary use case, a patient, or other stakeholder, is able to interact with a doctor's office via a Guardian Card. In this example, a patient checks into the doctor's office with their Guardian Card, which triggers numerous office visit events. First, the patient is authenticated. Further the patient's medical data stored on the Guardian Card can be downloaded or updated, if necessary or required. Second the cOS environment can verify that the patient data is accurate or verified (e.g., ability to pay, insurance coverage is valid, etc.). Third, the doctor's personal device (e.g., tablet, phone, etc.) can be updated with medical records of the patient. For example, in preparation for the visit, the doctor's device can establish, via a cOS agent, a secure container in memory of the device that stores the EMRs of the patient. The doctor can then access the patient's EMR data in a secure fashion.

Upon completion of the doctor's visit, the patient can check out of the doctor's office, possibly via swiping their Guardian Card on a docking station as illustrated. The act of checking out also triggers multiples actions. The Guardian Card can be updated with new EMR data, prescription information, or other visit data. Further, the cOS system can use account information stored in the Guardian Card to process payments, bill insurance, supply billing codes (e.g., CPT codes, ICD 9 codes, ICD 10 codes, DSM codes, etc.), update health spending accounts, or other actions.

Other exemplary use cases may be found outside of the health care context. For example, one exemplary use case of the invention is focused on an entertainment ecosystem. In this example, a consumer can interact within one or more kiosks or vending machines that are configured to provide digital content. The consumer can tap or present their Guardian Card to a card reader on the kiosk. Upon authentication or payment, the kiosk can send the digital content, perhaps a movie, to the card's memory. It should be appreciated that contemplated cards may transmit digital data via close proximity wireless communication interfaces at rates of up to 6 Gbps. Thus, a Blu-ray movie of about 25 GB may be transferred in less than 35 seconds; a time frame easily acceptable to a busy consumer. An acceptable wireless communication interface that would support such data exchanges includes those described in U.S. Pat. No. 8,554,136 to McCormack titled "Tightly-Coupled Near-Field Communication-Link Connector-Replacement Chips", filed Dec. 21, 2009; U.S. Pat. Nos. 8,714,459 and 8,757,501 to both to McCormack et al. and titled "Scalable High-Bandwidth Connectivity" filed May 14, 2012 and Mar. 4, 2013 respectively; U.S. Pat. No. 8,811,526 to McCormak et al. titled "Delta Modulated Low Power EHF Communication Link", filed May 31, 2012; and U.S. patent application publication 2014/0273856 to Kyles et al. titled "Extremely High Frequency Systems and Methods of Operating the Same", Mar. 13, 2014.

In addition to the scenarios described above, the Guardian Card may also be used to authenticate the consumer, grant rights to the digital media (e.g., DRM, etc.), secure transfer of the digital content, enforce DRM compliance, initiate or authorize transactions, update loyalty accounts, or in support of other actions. When the consumer is in a suitable venue, say at home, the consumer can dock their Guardian Card with their television or other media device, which in turn renders the content for consumption by the consumer.

The exemplary use cases described above clarify that the Guardian Card can store myriad types of a data beyond just EMRs or movies. Example types of digital data that may be stored in the card's memory includes at least one genome-based transaction token, healthcare data, genome data, image data, video data, audio data, application data, prescription data, medical record data, biometric data, patient data, hospital data, debit card data, credit card data, loyalty card data, insurance data, health spending account data, security data, authentication data, clinical operating system data, clinical data, pharmacy data, benefits data, historical data, doctor data, healthcare provider data, payment data, payor data, treatment data, prognosis data, diagnosis data, movie data, game data, authorization data, access level data, digital rights management data, compliance data, vending machine data, marketing data, family data, toy data, augmented reality data, green screen content data, television content data, product or service promotion data, streamed data, or other types of data or data modalities.

Another exemplary use case outside the health care context includes a vending machine ecosystem, somewhat similar to the movie exemplary use case described above, in which a consumer can use transaction cards to purchase physical products or other types of products. In this example, each vending machine can be instrumented with complementary card reading technologies; a magnetic strip reader, a contact pad reader, a wireless interface, etc. To purchase a product from the vending machine, the consumer docks their Guardian Card with the card reader of the vending machine. In response, the vending machine authenticates the consumer and processes payment, and then the vending machine can dispense a selected product.

Yet another exemplary use case for embodiments of the present invention that is peripheral to the health care context can include electronic children's toys. In this case, toys can be configured to interact with the Guardian Card. As a child interacts with the toy, the toy or other computing devices (e.g., phone, tablet, server, laptop, appliance, kiosk, etc.) can unlock features associated with the toy. A child can unlock augmented reality content that can be rendered on a tablet along with an image of the real-world object. As the child plays with the toys, their Guardian Card can take various actions possibly including recording the child's playing habits, unlocking DRM content, manage accounts (e.g., credit cards, loyalty, healthcare spending accounts, etc.), or other type of actions.

Consider a scenario where a child visits a doctor's or dentist's office. As a reward for the visit, the child's Guardian Card may be provisioned, via a cOS, with Disney® princess toy content rather than candy or stickers. When the child returns home, the child can place their Guardian card near an electronic Disney toy, perhaps a suitably configured Elsa@ Princess doll. In response, the doll may down load the new content from the Guardian Card and then present the content to the child. For example, the doll may now be provisioned with a new song, new actions assuming the doll is capable of electronic articulation, or other features.

With respect to imaging data, the disclosed techniques can also augment functional visualization and analysis software to benefit physicians, patients and healthcare specialists. The genome-based transaction devices provide a key for intuitive clinical tools across the enterprise. User needs for advanced visualization or analysis have changed over the past decade. These changes are addressed by providing clinicians access to tools based on transformational technology which removes the barriers of accessibility while maintaining performance and image integrity. The medical community lives in a challenging world filled with vast image data sets produced by a wide array of digital imaging modalities. Thousands of images per patient bring greater diagnostic capabilities, but also gives rise to complex, time-consuming image analysis and management needs. This is creating a far greater need for more accurate and efficient solutions as 3D advanced visualization alone becomes less sufficient. Not only are stakeholders able to access imaging data based on coupled genomic data, but also the imaging data itself can couple with the genomic data to function as a foundation for authentication or for gaining authorization.

Imaging techniques leveraging 4D advanced processing platforms offer an unprecedented "real-time" journey through the body non-invasively, supporting applications such as precise surgical and radiation therapy planning for a wide variety of organ targets—brain, lungs, heart and beyond, and thereby enabling appropriate, actionable outcomes across the patient continuum. The size of data set and the modality of imagery lend themselves to storage and transport using the high throughput techniques as describe with respect to the transaction devices. For example, in addition to storing whole genomes, the transaction servers or systems can also store or transmit massive imaging healthcare imaging files over wireless communication interfaces.

It should be appreciated that large file storage or massive numbers of files are also relevant to ecosystems beyond healthcare, while still being locked via the disclosed techniques. Videos and large file games are utilized to educate and entertain patients, employees, and children. These files will be transported and stored between keycards (e.g., genome-based transaction cards, wireless cards, USB cards, etc.), mobile devices, fixed kiosks, appliances, or other computing devices. Kiosks may house above content and may also deliver products at the point of interaction such as medications, pharmaceuticals, video content, financial transactions, or any products of use to the holder of a suitably configured enabled card or mobile device.

The disclosed transaction device can leverage numerous operating system ecosystem services both locally within the devices or deployed within the enterprise. Consider embodiments that leverage the QNX operating system within a BlackBerry® enterprise ecosystem. The disclosed transaction devices or system can integrate with BlackBerry Messaging (BBM) services. The security and reliability offered across all Blackberry platforms including QNX, encrypted video, messaging, voice systems are well suited for the disclosed environments. In order to integrate with the BlackBerry ecosystem, the disclosed devices, servers, or systems can standardize on the QNX kernel based OS. Regardless of the physical interface between the communication interfaces and the processor/storage (e.g. USB 3.0, PCIe, SATA, DisplayPort, etc.), the native detection of underlying communication interface is a useful functionality for security, reliability, and end-to-end performance of the interface. It should be appreciated that device drivers for proprietary communication interfaces can be foundational templates for use in other OSes. For example, QNX device drivers for the chips described in U.S. Pat. Nos. 8,554,136; 8,714,459; 8,757,501; 8,811,526; and U.S. patent application publication 2014/0273856 can serve as a template for VxWorks, Linux, or even Windows® operating systems.

The disclosed transaction devices also provide efficiency, efficacy, and security with respect to payment systems in many markets including a healthcare enterprise. For example, the genome-based transaction cards can represent implementations based on Payment Card Industry Data Security Standards (PCI DSS) framework published by the Security Standards Council (SSC). Further, the secure payment applications can be structured to comply with Payment Application Data Security Standard (PA-DSS) version 3.0. The secure data transfer from payment terminals to a cOS over high bandwidth wireless communications interface enables significant types of transactions that have not yet been seen. Standardization of such a mechanism of payment layered with HL7 medical data transfer as well as HIPAA compliant standards establish three layers of interface standards: the first mechanical/electrical, the second adding security and the third adding data transport protocols for medical devices (HL7), for HIPAA compliant records, for imaging data, for secure messaging.

The disclosed genome-based transaction devices can also take on different form factors beyond card-based form factors. In some embodiments, the genome-based transaction devices may also comprise a wrist band or a smart watch. Such wrist-based devices can comprise a wireless communication interface that allows the devices to interact with point-of-transaction devices, possibly based on close proximity. As discussed previously, the form factor embodiments for the transaction devices can also comprise mobile or portable devices, possibly including cell phones, smart phones, tablets, robots, phablets, game systems, game controllers, smart jewelry, toys, vehicles, drones, smart cloths, smart shows, AR or VR glasses, or other types of mobile devices.

It is also contemplated the form factor of the genome-based transaction device may take on the form of a child's toy. Children are likely to have one or more favorite toys, say a stuffed animal. The stuffed animal can comprises the computing device elements described with respect to trans-action device 110 in FIG. 1. For example, the stuffed animal can include a memory configured to digital genomic data, genome data structures, partitions, or other data related to the child's genome. Further the communication interface may include an NFC or other wireless interface located in the hand or appendage of the stuff animal. When the child is required to interact with a point-of-transaction device (e.g., a doctor's cell phone or tablet), the child can place the hand next to the receiving device to transmit authentication information. As the child becomes more sophisticated, their genomic-based authentication information can be transferred or copied to other devices (e.g., cell phones, ID tags or cards, etc.).

In yet another embodiment, the transaction device may comprise a smart wallet or e-wallet. The smart wallet may comprise a physical device having multiple interesting features in addition to those described above. For example, the smart wallet may include one or more pockets of various sizes for storing money, credit cards, or other traditional items. Further, the interior portion of the wallet may include a foldable e-paper or flexible display that can present a user interface to the user of the smart wallet. The consumer can access the memory, features, or apps of the smart wallet through the user interface presented on the display. The display can also be configured to present other information possibly including bar codes for account transactions, user identification, or other image-based data. Still further, the smart wallet can also include a wireless communication interface as discussed previously, which allows the smart wallet to interact with a point-of-transaction device. In some embodiments, the smart wallet can also include a retractable hard plastic card with a programmable magnetic strip or contact pads, which is configured to communicatively couple with traditional card readers. For example, a user may select a specific credit card account via the user interface on the display in the smart wallet, which in turn configures the programmable magnetic strip with selected account data (e.g., credit card number, loyalty card identifier, digital cash protocol data, etc.). As the user swipes the strip through the card reader, the reader can authorize the trans-action of interest using traditional protocols. The smart wallet can also transfer genomic-based authentication or authorization tokens via the magnetic strip, contact pads, or through wireless schemes discussed previously. It should be appreciated that such a smart wallet can be configured to exist within a personal area network ecosystem and may wirelessly couple (e.g., lower energy Bluetooth, WiGIG, etc.) with other personal devices including a smart phone, smart watch, sensors, smart rings, game systems, smart jewelry, smart cloths, toys, or other devices.

Smart wallets provide numerous advantages. Such smart wallets can retain features (e.g., pockets, money slots, etc.) that allow consumers to interact with the wallets in a traditional fashion. Additionally, smart wallets allow for aggregation of multiple identification cards including driv-er's licenses via the display, genomic authentication or authorization data as discussed above, healthcare cards, credit cards, loyalty cards, membership cards, debit cards, photos, insurance cards, or other types of identification. Still further, the smart wallet can store additional data beyond cards or genomic-data. For example, the smart wallet may also store digital cash, digital money, cryptocurrencies (e.g., BitCoin, LiteCoin, PeerCoin, DogeCoin, etc.), or other monetary data. As the smart wallet, or other transaction devices storing such e-currency, interacts with point of transaction devices, the smart wallet can be configured to engage the point of transaction devices via complementary protocols.

Beyond healthcare, the disclosed transaction devices can impact other markets, such as the entertainment market. The transaction devices can be also be configured with additional memory, if necessary, that enable the transaction devices to acquire or store digital content. For example, the transaction devices can authentication a purchase of a digital movie (e.g., HD movie, 4K Ultra HD movie, 8K content, etc.) or other types of content. Such digital content can then be transferred from a point of transaction to the transaction device. Consider the purchase of a 4K movie, which may be about 160 GB in size. Such a movie may be transferred to the transaction device via a wireless communication inter-face as discussed above in less than four minutes. Other types of digital content that can be stored on the transaction devices beyond movies include music data, video data, image data, digital books, digital broadcasts, streamed con-tent, games, applications, or other types of digital content. Thus, digital content can be stored, rendered, transported, distributed, synchronized, or otherwise managed via the disclosed techniques based on required, possibly genomic-based, authentication.

In view that the disclosed transaction devices are able to interact with a point-of-transaction device with very low latency and high bandwidth (e.g., more than 6 Gbps), the disclosed approaches gives rise to additional opportunities in the market. For example, a transaction server (see transac-tion server 340 in FIG. 3) may comprise a vending machine or even a gas station pump that also operates as a point-of-transaction device. A consumer may "dock" their transaction device with the vending matching, possibly via a wireless or NFC communication interface. Once the consumer has been authenticated and a purchase transaction is complete as discussed previously, the vending machine can transfer purchased digital content (e.g., movies, music, etc.) via the communication interface directly to the transaction device.

Further, a similar type of transaction server to the vending machine may also operate as an information hub in a healthcare environment. For example, in a hospital ecosys-tem, terminals (e.g., kiosk, dumb terminal, etc.) may be disposed about the floors of the hospital. Each terminal can comprise a communication interface and operate as an EMR or EHR transaction server. As a doctor or other caregiver makes their rounds, the caregiver can dock their smart phone or tablet operating as a transaction device with the terminal. Upon completion of required authentication, the terminal can upload patient records or other data to the caregiver's device in support of their rounds.

Embodiments of the invention thus enable construction or configuration of one or more computing devices to operate on vast quantities of transactional digital data, beyond the capabilities of a human. Although the transactional digital data represents various forms of transaction data, it should be appreciated that the digital data is a representation of transactional information and not the abstract concept of the transaction per se. By instantiation of such digital models or data structures in the memory of the computing devices, the computing devices are able to manage electronic transaction in a manner that may provide utility to a user of the computing devices that the user would lack without such tools.

Embodiments of the invention discussed previously include transaction cards or devices that allow consumers to conduct electronic transaction via a single, unitary device, possibly based on personalized genomic data. The devices disclosed below expand on the previously disclosed concepts by focusing on how such devices can augment consumer management of accounts, whether they are owned by the consumer or owned by a different entity, as well as providing discovery opportunities for new services or products.

Figure 7:
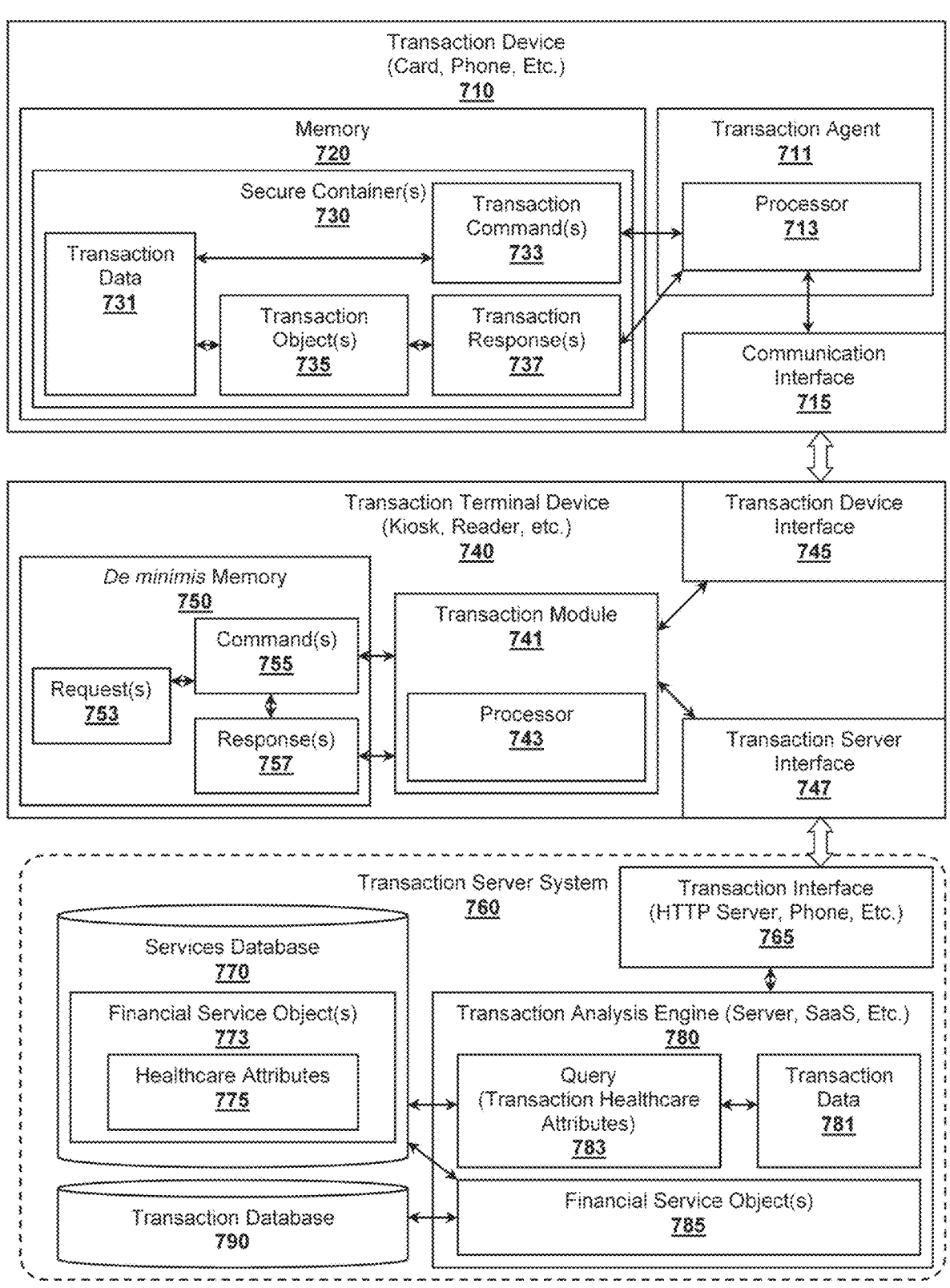
FIG. 7 illustrates a block diagram of an exemplary distributed computer system including an exemplary transaction device, an exemplary transaction terminal device, and an exemplary transaction server system that can implement one or more aspects of a transaction analysis engine in accordance with an embodiment of the present invention.

FIG. 7 illustrates a network environment for a transaction comprising transaction device 710, transaction terminal device 740, and one or more of transaction service system 760. In this ecosystem, transaction device 710 is configured or programmed to provide transaction services not only for accounts owned and managed by the consumer but also for accounts owned or managed by remote entities possibly operating account or data custodian servers (not shown). It should be appreciated that in the disclosed transaction model that processing of transactions, especially healthcare transactions, can occur locally on transaction device 710 in lieu of or in addition to the remote account servers. Transaction server system 760 may operate as an account server. However, transaction server system 160 is intended to represent an analysis system that monitors or observes transactions with a goal of providing opportunities for discovering new or relevant services that may benefit the consumer or other stakeholders.

Transaction device 710 as illustrated builds on the concepts presented in the companion documents referenced previously and comprises memory 720, processor 713 (e.g., single core, multi-core, cryptographic support chips etc.), communication interface 715, and transaction agent 711. Although not shown, transaction device 710 can also be provisioned with one or more operating systems (e.g., QNX®, VxWorks®, Linux®, IOS®, Android®, etc.), which provide supporting services for higher level functionality such as those provided by transaction agent 711. Transaction device 710 can comprise different form factors including a mobile device (e.g., smart phone, tablet, phablets, game console, etc.), or even a housing with a credit card form factor that houses the elements of transaction device 710.

Memory 720 preferably comprises a comparatively large capacity and can comprise solid state memory, perhaps a solid state disk (SSD). For example, memory 720 may comprise the Samsung SSD 840 EVO or the Crucial M550 SSD, both of which comprises roughly 1 TB of capacity. Other types of memory include Flash, nvRAM, nvSRAM, FeRAM, MRAM, PRAM, or other non-volatile memory. Providing a large capacity for memory 720 allows transaction device 710 to store vast quantities of disparate data including genomic information (e.g., whole genomes, tokens, differences, BAM files, BAMBAM files, etc.), medical records, digital content (e.g., movies, videos, games, applications, etc.), medical history, cryptocurrencies or other digital cash, or other types of digital data.

Memory 720 has been provisioned with one or more of secure container 730 that is configured to store various aspects of data in support of an electronic transaction. Secure container 730 can take on my different forms. More preferred secure containers 730 represents portions of memory that are encrypted according to one or more token, possibly based on genomic data as discussed in the companion documents. In more specific embodiments, secure container 730 may be instantiated via techniques such as those provided by VeraCrypt (see URL veracrypt.codeplex-.com) or BitLocker® where a partition of memory 720 can be encrypted multiple times. Example cryptographic algorithms that can be used to instantiate secure container 730 include AES, 3DES, RIPEMD160, SHA-2, Whirlpool, or other algorithms known or yet to be invented. Still further, secure container 730 can comprise a FIPS 140 compliant memory.

Although one of secure container 730 is illustrated, it should be appreciated that transaction device 710 can be configured with multiple instances of secure container 730 where each instance may be allocated to a specific type of transaction, account, or service. For example, a first instance of secure container 730 might be dedicated to a health spending account (HSA). The HSA account container can store transaction data (e.g., balances, historical records, etc.) in support of the HSA transaction activities. Such dedicated secure containers 730 can be secured with more than one token. In the example of the HSA secure container 730, data stored in the container might be secured based on consumer token (e.g., password, genomic string token, etc.) as well as a key or token provided by the HSA management entity (e.g., bank, insurance company, etc.). When both tokens are provided to transaction agent 711, the HSA secure container can be unlocked. This approach is considered advantageous because it allows transaction device 710 to be a centralized hub or nexus for consumer data while also enforcing ownership rights of other stakeholders.

In some embodiments, secure container 730 comprises an implementation of a file system, preferably a secured file system. Example file systems that can be deployed within transaction device 710 include NTFS, FAT, exFAT, F2FS, FSFS, SFS, ZFS, ext3, ext4, DataPlow® SFS, or other file systems. Journaling file systems are more preferred to ensure data integrity is retained should a disruption in processing occur.

Secure container 730 can also be a storage facility for a homomorphic transaction session. For example, should the consumer engage with multiple healthcare entities, transaction agent 711 can establish a homomorphic encrypted session among the entities, thus preserving confidentiality, while also providing access to secure container 730 for storing or processing transaction data 731 during a healthcare transaction (e.g., exchange of records, making payments, distributing payments among stakeholders, etc.). In such scenarios, secure container 730 comprises a homomorphic encrypted container.

Communication interface 715 comprises one or more physical elements (e.g., connectors, wireless chip sets, antenna, etc.) that are configured to provide digital or electronic communication between transaction device 710 and an external device, transaction terminal device 740 for example. More preferred embodiments comprise point-to-point connectivity. Example wired communication interfaces include a contact pad, a USB connector, an Ethernet connector, a Firewire connector, or other connector. In more preferred embodiments, communication interface 715 includes wireless connectors, possibly including a wireless USB interface, a WiGIG interface, a WiFi interface, a Zigbee interface, a Bluetooth interface, a 60 GHz interface, an NFC interface, a TransferJet interface, or other interface. More specific examples of a suitable wireless 60 GHz interface are described in U.S. Pat. No. 8,554,136 to McCormack titled "Tightly-Coupled Near-Field Communication-Link Connector-Replacement Chips", filed Dec. 21, 2009; U.S. Pat. Nos. 8,714,459 and 8,757,501 to both to McCormack et al. and titled "Scalable High-Bandwidth Connectivity" filed May 14, 2012 and Mar. 4, 2013 respectively; U.S. Pat. No. 8,811,526 to McCormack et al. titled "Delta Modulated Low Power EHF Communication Link", filed May 31, 2012; and U.S. patent application publication 2014/0273856 to Kyles et al. titled "Extremely High Frequency Systems and Methods of Operating the Same", Mar. 13, 2014.

Transaction agent 711 is configured or programmed according to software instructions stored in memory 720 and where the transaction agent 711 executes on processor 713 or at least one of its cores. Only one of transaction agent 711 is illustrated in FIG. 7. Still, it should be appreciated that more than one of transaction agent 711 may exist within transaction device 710. In some embodiments, transaction agent 711 can be instantiated in support of one or more transactions where each transaction agent 711 might correspond to or be bound to one or more instantiated secure container 730 in support of the transaction. In some embodiments, transaction agent 711, processor 713, and memory 720 may be implemented with a programmable gate array.

Transaction agent 711 can be implemented through various techniques. In some embodiments, transaction agent 711 is a virtual machine executing on processor 713, possibly under control of a remote account transaction server based on transaction commands 733. In other embodiments, transaction agent 711 can comprises one or more stand-alone apps or applications that process transaction data. Depending on the nature of transaction agent 711 and its goals with respect to the electronic transaction, transaction agent 711 can take on various roles or responsibilities with respect to transaction data 731.

Transaction data 731 can include a wide variety of data types associated with one or many possible transactions. For example, transaction data 731 may include data associated with a specific bank account or HSA account; an account balance for example. Further transaction data 731 might include purchased content or even EMR data. Thus, transaction data 731 may include or more of an electronic medical record, an electronic health record, a payment amount, loyalty program data, genomic data, application data, an application, a currency, a digital currency, a cryptocurrency, a promotion, an advertisement, game data, video data, image data, transaction support modules or libraries, healthcare block chains, or other types of data in support of the transaction.

In some especially preferred embodiments, transaction data 731 may include digital models of a patient's tissues; heart, lung, kidneys, brain, etc. The digital model can include tissue characteristics, deformable registration of images, movement models, tissue or organ kinematics, mechanical properties (e.g., shear, stress, strain, resilience, etc.), or other properties. Such an approach provides for storage of highly personalized digital models of the patient's body, organs, tissues, cells, or even genomes. Example techniques for modeling the human heart are described in "Custom Cardiology: A Virtual Heart for Every Patient", IEEE Spectrum, Oct. 28, 2014, by Natalia Trayanova (see URL spectrum.ieee.org/biomedical/imaging/custom-cardiology-a-virtual-heart-for-every-patient/?utm_source= techalert&utm_medium=email&utm_campaign=103014).

Transaction agent 711 is configured or programmed to receive transaction commands 733 via communication interface 715 and that are related to an electronic transaction. Transaction commands 733 can be received via one or more protocols implemented in transaction agent 711. In more preferred embodiments, the protocols comprise standardized protocols. For example, transaction commands 733 may be transmitted to transaction agent via TCP/IP, HTTP, HTTPS, or other digital protocols. Further, transaction commands

733 may be encoded within a serialized structure; XML or JSON for example. In other embodiments, the transaction commands 733 can be packaged within secured financial protocols; FIX for example.

Transaction commands 733 can comprise quite a large spectrum of commands to support the transaction, again, depending on the scope of responsibilities associated with transaction agent 711. In more preferred embodiments, transaction commands 733 can be considered one or more transaction modules that include executable code within transaction agent 711. In a very real sense, one can consider the combination of transaction agent 711 along with transaction commands 733 as an extension of the application or operating system executing on a remote transaction account server or even transaction server system 760. This approach is considered advantageous because it allows an entity that owns an account or its corresponding data to control transaction processing on transaction data 731 while also allowing the consumer to retain access to their complete data set on transaction device 710.

In some embodiments, transaction commands 733 may comprises compiled code, binary instructions, scripts (e.g., Python, Ruby, Lua, Java, etc.), byte codes (e.g., MSIL, Java bytecodes, etc.), compiled modules, compiled libraries, applets, apps, applications, or other form of executable code. Consider a scenario where transaction agent 711 comprises an instantiated virtual machine executing on processor 713 and dedicated to a specific transaction. Transaction agent 711 can include a launched run-time, say Java, which receives a Java application (i.e., transaction commands 733) via communication interface 715 and launches the application, subject to proper authentication or authorization. The Java application may include support for the FIX protocol or other transaction protocols in order to execute transaction processing locally within transaction device 710. It should be appreciated that transaction commands 733 may relate to many different types of transactions, especially in view that the large portions of transaction processing may occur locally. Thus, transaction commands 733 may comprise high level instructions (e.g., scripts, etc.) or low level instructions (e.g., compiled code, etc.) associated with nearly any type of transaction, including a healthcare data transaction, a payment, a loyalty transaction, an account transaction, a debit transaction, a credit transaction, a financial service transaction, a banking service transaction, a health spending account transaction, a flexible spending account transaction, or other type of transaction.

Transaction agent 711 executes transaction commands 733 on transaction data 731 to process at least a portion of the electronic transaction locally within transaction device 710. Through execution of transaction commands 733, transaction agent 711 instantiates one or more transaction objects 735 representing data constructs representing the results of the transaction processing. For example, transaction agent 711 may be instantiated to process an authentication request based on a key exchange. In such a case, transaction commands 733 would likely include instructions for executing one or more hash or cryptographic algorithm implementations on keys or tokens within transaction data 731. The results of the hash or cryptographic algorithm implementations would be transaction object 735.

In embodiments where transaction data 731 comprises digital models of a patient's heart or other body part, transaction commands 733 can include instructions to execute or simulate the corresponding patient's body part. Thus, transaction object 735 might include an executing simulation. For example, transaction agent 711 may execute a simulation of a patient's lungs under respiration with modifications suggested by transaction commands 733 (e.g., scar tissue from surgery, sutures, etc.). In such cases, the simulation may be controlled or operated by the remote servers. Alternatively, transaction objects 735 may comprise a packaged module including the model or models. The package module can be sent to the remote servers where the models may be simulated remotely.

In response to the generation of one or more transaction objects 735, transaction agent 711 further generates transaction response 737 from the transaction objects 735. Transaction response 737 represents the final form of the data that adheres to the transaction protocol under which transaction agent 711 is operating. For example, returning the example of authentication, transaction response 737 would comprise the protocol response (e.g., Keberos, RADIUS, etc.). Finally, transaction agent 711 packages transaction response 737 for transmission to an external device via communication interface 715. The external device may include transaction terminal device 740, an account or transaction server, transaction server system 760, or other device involved with the electronic transaction.

Transaction device 710 provides numerous advantages. Transaction device 710 can be considered a fully connected device capable of interacting with numerous other electronic devices over network connections in support of conducting transactions. Consider an embodiment where transaction device 710 comprises a card form factor (e.g., healthcare card, credit card, etc.). The card may be considered a universal card that allows consumers to carry fewer cards while also ensuring the consumer remains in control over their security concerns. The card would integrate naturally with existing transaction systems (e.g., on-line banking, ATMs, loyalty cards, gift cards, membership cards, driver's licenses, passports, etc.). Further, in embodiments where communication interface 715 provides for longer range connectivity possibly in addition to a point-to-point connectivity, the card can serve as a central hub for a personal area network. In such cases, the card may provide an external memory for sensor devices by storing sensor data within a personal area network (PAN). Further, then card may also provide computational support for other PAN devices (e.g., cell phone, tablets, wearable devices, sensors, electronic clothing, etc.). Example computational support may include providing an execution runtime for an application, operate as a PAN web server or service platform, PAN storage, encryption, a command and control hub for nearby devices, a second display in embodiments where transaction device 710 includes a display, or other types of computational services.

Transaction device 710, especially within a card form factor, can be considered a universal card that operates as the nexus point for many different types of transactions. In view the that card may include quite a large amount of private data, possibly owned by the consumer or owned by other entities, security is very important. Further, card management is also very important. In some embodiments, the contents of memory 720 can be mirrored on remote data stores, possibly located at transaction server system 760. In addition to or alternately, portions of memory 720, one or more of secure containers 730 for example, may be mirrored across the participating entities that might own transaction data 731 associated with their secure containers 730. In such a case, the collection of data stored at the remote entities' servers can be linked together via pointers or other references (e.g., DOI, URLs, network address, torrent address, etc.). Such an approach allows for construction of a new card or reconstruction of a card should the card be lost or stolen.

As discussed previously, security features may include ensuring that secure container 730 complies with FIPS 140 or other security standard. Further, data can be secured through multiple layers of encryption such as those provided by VeraCrypt. For example, a current version of VeraCrypt, version 7.0e at the time of this writing, supports over 500,000 iterations of RIPEMD160, SHA-2, and Whirlpool, which provides for enhanced security and makes it much harder for an attacker to gain access to transaction data 731 through a brute force attack. Although the number of iterations can incur latency, the amount of time incurred on a transaction basis is considered within an acceptable delay budget of a consumer at a point of transaction.

Cards can be managed through transaction commands 733. For example, transaction commands 733 can include a set of commands that focus on management of the card itself. Card management commands may include one or more of a NULL command, a wipe command, a mirror command, a synchronization command, a clone command, a copy command, an activate command, a deactivate command, a configuration command, an account management command, a re-encrypt command, an overwrite or replace command, a provisioning command, a backup or distribute command, or other command affecting the operation of the card.

Transaction device 710 can be configured to interact with a point-of-transaction device represented by transaction terminal device 740. Transaction terminal device 740 can include a kiosk, a cash register, a card reader, a cell phone with a card reader (e.g., Square®, PayPal Here™, etc.), a mobile device with an NFC interface, an appliance, a game system, a docking station, a dumb terminal, or other type suitably configured electronic device. Further, transaction terminal device 740 may comprise a suitably adapted Poynt™ point-of-sales terminal (see URL getpoynt.com) having a 60 GHz interface or enabled with a transaction broker module app as discussed below. Transaction terminal device 740 can comprises a minimal computing device having minimum sufficient computing resources to broker an electronic transaction between transaction device 710 and a remote server; transaction server system 760 in some cases. Transaction terminal device 740 includes de minimis memory 750, processor 743, transaction device interface 745, and transaction server interface 747. Transaction terminal device 740 further comprises transaction broker module 741, which has the actual brokering responsibilities.

De minimis memory 750 represents physical memory sufficient for transporting or tunneling transaction information from the remote server to transaction device 710. Although de minimis memory 750 is referenced as de minimis, it should be appreciated the term is used euphemistically to indicate that de minimis memory 750 can be quite lean and to indicate that transaction broker module 741 may include minimal capabilities. For example, de minimis memory 750 might comprise just enough capacity to store the software instructions supporting transaction broker module 741 and communication buffers for transporting data messages across transaction device interface 745 and transaction server interface 747.

Transaction broker module 741 is configured or programmed according to software instructions in de minimis memory 750 to execute on processor 743. Transaction broker module 741 is configured to receive transaction request 753 from at least one of transaction device interface 745 or transaction server interface 747. For example, a consumer might use a card version of transaction device 710 to check-in at a healthcare facility where transaction terminal device 740 comprises a docking station or card reader. Initially, transaction request 753 might include a patient token (e.g., genomic sequence, patient id, etc.) obtained from the card via transaction device interface 745; a contact pad interface, or 60 GHz NFC interface for example. Another preferred type of interface includes those that adhere to Europay, MasterCard and Visa (EMV) standard. Once the patient is authenticated, the next transaction request 753 might include a request for EMIR data located on the patient's card where the second transaction request 753 is obtained from a remote server via transaction server interface 747 over a network (e.g., Internet, PSTN, ATM, LAN, WAN, etc.), possibly from transaction server system 760.

In more preferred embodiments, transaction device interface 745 takes on the form of an interface complementary to communication interface 715. For example, transaction device interface 745 may also include a 60 GHz wireless chip set that provides high bandwidth, proximal communications. Other types of interfaces may include a contact pad, a card reader, a USB connector, WiFi interface, Bluetooth® interface, or other local interfaces. Transaction server interface 747 may be take on different forms as well depending on the nature of the communication network between transaction terminal device 740 and remote account servers of transaction server system. Example transaction server interfaces 747 may include 802.11, Ethernet, PSTN, or other type of network interface.

Transaction broker module 741 is also configured to generate at least one transaction command 755 based on the transaction request. It should be appreciated, that transaction command 755 may comprise transaction request 753 itself especially in embodiments where transaction terminal device 740 is a minimal participant in the ecosystem. Transaction broker module 741 transmits transaction command 755 to transaction device 710 via transaction device interface 745. Thus, transaction command 755 may correspond to transaction commands 733. In response, transaction broker module 741 receives transaction response 757, which may correspond to transaction response 737 and then can transmit transaction response 757 to the remote external device or other transaction server via the transaction server interface 747.

Transaction broker module 741 can be configured or programmed to operate as a tunnel between transaction device 710 and the remote transaction server. In such embodiments, transaction terminal device 740 may be considered transparent to the transaction server and transaction device 710. For example, transaction broker module 741 can buffer transaction commands 755 from the transaction server and submit them directly to transaction device 710. More specifically, transaction broker module 741 may receive transaction commands 755 via a TCP/IP session or UDP/IP connection from the transaction server. Upon reading the commands from the message buffer, transaction broker module 741 configures transaction device interface 745 to transmit the commands on to transaction device 710. The approach to providing a simple transaction tunnel through transaction terminal device allows the remote transaction server to control or otherwise command transaction agent 711 especially in situations where the remote transaction server has rights to transaction data 731, while the consumer does not.

In the disclosed ecosystem, transaction terminal device 740 brokers electronic transaction between transaction device 710 and a remote transaction or account server (not shown). In addition, the ecosystem also includes one or more of transaction server system 760, which monitors or otherwise observes the electronic transactions flowing through the ecosystem. Transaction server system 760 has the responsibility for adding value to the overall transaction processing by tracking trends or other aspects of the transaction flow in order to provide insight into relevant financial or other transaction services, especially within a healthcare environment. The following discussion describes transaction server system 760 from the perspective of healthcare as an example.

Transaction server system 760 includes services database 770, which is configured or programmed to store financial service objects 773. Financial service objects 773 comprises data that represents a corresponding financial service, product, financial service provider, or other item associated with transaction management. For example, financial services object 773 can include a description of the product, a product identifier (e.g., GUID, version number, SKU, etc.), one or more executable modules configured to generate a recommendation with respect to observed transactions, or other information. In more preferred embodiments, financial service objects 773 further comprises healthcare attributes 775 that indicate healthcare circumstances or healthcare contexts for which the corresponding service or product is considered relevant. Healthcare attributes 775 can adhere to an a priori defined healthcare namespace or ontology. Thus, financial service objects 773 may be considered as indexed according to the health context in which such services or products are considered relevant. Healthcare attributes 775 may be stored as a vector of data, where each dimension of the vector corresponds to a dimension of the healthcare namespace. If the dimension in not revenant to the financial services object 773, then the corresponding data value in the vector may take on a value of NULL indicating the lack of relevance of the dimension. Example types of database infrastructure that may be used for services database 770 include MySQL, PostgreSQL, Oracle, Microsoft SQL, Neo4J, or other types of database. Further, services database 770 may comprise a data structure stored in memory, possibly a kNN tree.

Healthcare attributes 775 can be take on a broad spectrum dimensions. From a financial perspective, healthcare attributes 775 might include healthcare payment data indicating costs associated with services or products. Further, the healthcare payment might indicate charges incurred by past patients or consumers. Similarly, healthcare attributes may also include health finance data representing a healthcare account balance, credit, or debit. Example healthcare account includes flexible spending accounts, healthcare spending accounts, insurance accounts, or other types of accounts.

Transaction server system 760 further includes transaction interface 765 that is configured to couple with external devices, including transaction terminal device 740 or even transaction device 710 for example. In some embodiments, transaction interface 765 comprises an implementation of an HTTP server that brokers HTTP-based transaction data (e.g., XML, JSON, WSDL, SOAP, HTTPS, HTML, etc.) between transaction analysis engine 780 and the external devices. In other embodiments, especially embodiments where transaction server system 760 operates as an account management server (e.g., credit card server, payment account server, etc.), transaction interface 765 may comprise a PSTN interface that accepts data via phone lines. Transaction interface 765 has the responsibility of receiving digital transaction data 781 for transaction analysis engine 780.

Transaction analysis engine 780 comprises a computing device configured or programmed to provide healthcare services discovery opportunities based on monitoring or observing transaction data 781. In various embodiments, transaction analysis engine 780 can comprise a server that offers its services over a network (e.g., LAN, WAN, PAN, Internet, intranet, etc.), possibly as a SaaS, PaaS, IaaS, or even a cloud-based implementation.

Transaction analysis engine 780 is configured to receive transaction data 781 via transaction interface 765. For example, transaction data 781 might comprises transaction response 757 or 737 from the external devices. Transaction data 781 can comprises a serialized data structure (e.g., XML, JSON, YAML, etc.) that includes the parameters describing the nature of the corresponding transaction (e.g., transaction identifier, initiator identifier, destination identifier, account identifier, transaction objects, time stamps, costs, charges, device context attributes, healthcare information, etc.).

Transaction analysis engine 780 is further configured or programmed to derive transaction healthcare attributes from transaction data 781. In some embodiments, the transaction healthcare attributes might already be present in transaction data 781. For example, the transaction data might include a healthcare provider identifier, patient identifier, procedure codes (e.g., CPT codes, ICD codes, DSM codes, HCPCS codes, etc.), genomic data, or other healthcare related information. In such embodiments, the transaction healthcare attributes can comprise a one-to-one mapping from the healthcare information.

In other embodiments, transaction healthcare attributes can be inferred from transaction data 781. Consider a scenario where the transaction data 781 comprises an address of a pharmacy and a credit card charge. The transaction healthcare attributes might be derived by transaction analysis engine 780 inferring that the patient has filled a prescription, assuming no product information is available. The inference might also include one or more weighting factors indicating the strength or confidence of the inference, possibly based on empirically derived parameters. The transaction healthcare attributes can be normalized according to the common healthcare namespace used to define healthcare attributes 775.

Transaction analysis engine 780 is also configured or programmed to generate query 783 that targets the indexing schema of services database 770 and derived from the transaction healthcare attributes. For example, query 783 may comprise a vector where the members of the vector reflect the values of the transaction healthcare attributes. Thus, query 783 may be considered the current, inferred healthcare context of the transaction being processed. In additional embodiment, query 783 may comprises more complex nature including Boolean logic, keywords, SQL commands, or other structures that can be processed by services database 770.

Transaction analysis engine 780 uses services database 770 to identify a results set having zero or at least one of financial services object 785 having healthcare attributes 775 satisfying query 783. For example, query 783 might include multiple criterions with conditional logic related to healthcare attributes 775. Query 783 might include a criterion that requires a healthcare attribute associated with heart rate that falls within the range of 45 to 64. In which case, the financial services object 785 would have healthcare attributes 775 that likely include heart rate and have values in the indicated range. Further, if query 783 comprises a vector, then financial services object 785 might have healthcare attributes 775 that are considered to have a similarity measure that falls within a threshold value. For example, a Euclidean distance or Hamming distance may serve as a similarity measure. Upon identification of one or more of financial service objects 785, transaction analysis engine 780 further configures a device (e.g., cell phone, transaction device 710, transaction terminal device 740, etc.) to present financial service object 785, possibly as a recommendation.

It should be appreciated that transaction analysis engine 780 is able to provide discovery opportunities for financial services or products that may be consider contextually relevant to healthcare transactions as transaction data 781 flows through the ecosystem. As consumers or patients engage with healthcare entities via healthcare transaction, the patients or consumers can be notified of available services. Further, financial institutions or other entities (e.g., banks, credit card companies, companies having loyalty programs, etc.), can be notified when consumers might be interested in the institution's services or products based on the healthcare context, assuming the consumers authorize such information sharing.

Transaction server system 760 can further include transaction database 790 configured to store historical transactions. The historical transactions can also be stored according to or annotated with healthcare attributes for which the historical transactions pertained. In some embodiments, the historical transaction object may include more than one set of healthcare attributes. A first set may comprise the actual healthcare attributes that were validated as being relevant to the corresponding transaction. For example, after the transaction is completed, the corresponding historical transaction object can be tagged with or annotated with a validated healthcare context defined in terms of healthcare attributes, more preferably healthcare attributes from the common namespace or ontology. A second set of healthcare attributes may include the healthcare attributes inferred by transaction analysis engine 780 when the transaction was being observed. This approach is considered advantageous because it allows transaction analysis engine 780 to learn how to weight attributes in order to generate better discovery opportunities based on the differences between the two tests of healthcare attributes.

Transaction analysis engine 780 can be further configured or programmed to establish correlations between the historical transactions and the transaction data based on the transaction healthcare attributes. In some embodiments, transaction analysis engine 780 includes one or more correlation modules that operate according an implementation of multivariate analysis, Pearson correlations, support vector machines, or other techniques. In such embodiments, the historical transactions can also have healthcare attributes that satisfy similarity criteria defined by the base on the healthcare attributes 775 of financial service objects 773. This approach allows transaction analysis engine 780 to find historical transactions that might be relevant to the current context and may influence the result set of query 783.

In view that transaction server system 760 is able to track historical transactions, especially with respect to relevant healthcare attributes or healthcare contexts, transaction analysis engine 780 can be further configured to establish trends. Thus, an especially preferred type of healthcare attribute comprises trends. The trends may include a healthcare trend, a specific consumer trend, a specific patient trend, a demographic trend, a transaction trend, an insurance trend, a health account trend, a healthcare provider trend, or other types of trends. Though observation of trends, transaction analysis engine 780 can also determine if a transaction participant is deviating from a nominal or baseline trend. Such deviations can be indicative of an anomaly with respect to expected behaviors. These anomalies can be used to configure transaction analysis engine 780 with one or more alert criterion, which can be used to trigger alerts for activities that require more specific attention. For example, an anomaly with respect to a patient's nominal healthcare activity, perhaps visiting a different doctor, might indicate fraud.

The disclosed techniques give rise to numerous advantageous, especially within the scope of healthcare. For example, the ecosystem discussed above provides for or integrated health account management system able to process all transactions with respect to a patient's or consumer's health needs. Consumers or other stakeholders are able to efficiently make payments, process claims, bill other entities, or otherwise interact at a transactional level with each other. Such a collaboration further enables various specialists (e.g., in finance, in healthcare, in business, in banking, etc.) to deliver better solutions to the consumer because the specialists gain a deeper understanding of how their specific transactional services or products impact the healthcare of the consumer or the industry at large.

Consider a scenario where transaction device 710 comprises an electronic smart card. The card may operate as a single payment vehicle across the entire healthcare ecosystem while also providing storage for patient data (e.g., EMRs, EHRs, history, etc.) or other types of data or content. Further, the data stored on the card can remain under management or control of each owning entity through use of strong encryption. Thus, a patient is able to seamlessly move from one healthcare point-of-interaction to another via their card. For example, each entity in a chain of healthcare interactions (e.g., doctor's office, pharmacy, hospital, insurance, etc.) may be provisioned with simple terminals or docking stations operating as transaction terminal device 740.

Additionally, in embodiments where transaction device 710 allows remote servers to access secure container 730 (e.g., transaction agent 711 can be instantiated and controlled by transaction analysis engine 780), the remote servers can reach out to individual transaction devices in support of further analysis. For example, transaction analysis engine 780 might represent a server operating as a data custodian in a clinical operating system (cOS). As stakeholders query the cOS server, if necessary, the server could create a secure tunnel through transaction terminal device 740 to transaction device 710 to allow the cOS server to access transaction data 731 directly. Thus, the back-end analytics system is able to access remote data, subject to proper authorization, to generate responses to the queries. It should be appreciated that such queries can be cached or processed in batch until a connection is established between transaction device 710 and transaction server system 760.

The disclosed subject matter gives rise to numerous interesting capabilities. One interesting aspect is the disclosed genome-based transaction card can be provisioned based on direct input from a sequencing device. For example, the whole genome can be sequenced using one or more of the sequencing devices offered by Illumine® (see URL www.illumina.com). Alternatively, genomic information can be generated from portable device, possibly including the Oxford Nanopore™ MinION™ device (see URL www.nanoporetech.com).

Further, the disclosed transaction devices can support numerous healthcare informatics to create a convergence of a wide range of digital technologies to transform scientific research and healthcare, and to build an integrated evidence-based, personalized approach to the delivery of care and the development of next generation diagnostics and therapeutics.

Disclosed transaction cards can comprise a wireless connectivity system to enable the transport and storage of data including universal secured person identifier (e.g., genomic data, personalized images, etc.), the rapid upload storage or transfer of any information between patients, health care providers, pharmacies, payors, or other stakeholders. This ecosystem is integrated and interconnected by a mobile, fixed, or cloud-based informatic devices. This integrated informatic system transports medical, genomic, image, laboratory, payment, or other data securely across hospitals, clinics, or homes on one hand and a plethora of medical entities, systems, or processes on the other. The latter includes clinical research, pharmaceutical trials, medical and pharmaceutical delivery systems, radiology systems, imaging (e.g., x-ray, MRI, ultrasound, videos, etc.) systems, health records including electronic medical records and personal health records, Rx protocols, biometric signals and status, or payment systems for payors, payees, or providers. The underlying platforms to move, store, and transport such data include network connected mobile devices (e.g., smart phones or wearables), transaction devices, portable devices, fixed kiosks, tablets, personal computers, servers, supercomputers, storage computers and direct integration into medical equipment and medical diagnostic devices, whether through wireless network connection, Ethernet cabling, or other interconnections of some or all such equipment above in a networked environment.

The networked environment can also include a secure platform. Back-end systems, including the disclosed transaction server and authentication servers, are designed to be accessible from anywhere, and support medical and wellness device integration, genomic proteomic data, imaging systems, electronic medical records, patient health records, scheduling systems, patient accounting, pharmacy benefits management, lab data, pharmacy data, or other information systems.

One should appreciate that the disclosed techniques provide many advantageous technical effects including allocating memory to store secured digital data and to enable two or more computing device to participate an authorized electronic transaction, possibly over a network. Further, the secured digital data is instantiated in the memory of at least one of the computing devices in manner that causes the secured digital to appear as natural genomic information.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Additional Embodiments

A first additional embodiment of the invention is a device for initiating a digital genomic data-based transaction comprising a communication interface; a non-transitory computer readable memory storing a genomic data structure having digital genomic data representative of an entity's genome; and a transaction processor coupled with the communication interface and memory. The transaction processor can be configured to identify a partition of the genomic data structure based on a transaction request; derive a digital transaction token from the digital genomic data within the partition; and enable an electronic transaction as a function of the digital transaction token with an external device and responsive to the transaction request via the communication interface.

A second additional embodiment of the invention includes a transaction server comprising a communication interface, a processor and a memory. The communication interface is configured to communicatively couple with external computing devices over a network. The memory is configured to store instructions for an authentication agent. The instructions for the authentication agent, when executed by the processor, cause the processor to perform receiving a digital genome-based token and a digital image-based token via the communication interface from at least one external device; storing the digital genome-based token and the digital image-based token in the memory; linking the digital genome-based token and the digital image-based token to a transaction object relating to a transaction associated with the at least one external device; generating an authentication query related to the transaction object as function of at least the digital genome-based token and the digital image-based token; submitting the authentication query to a genome-based authentication server via the communication interface; receiving an authentication token related to the transaction object from the genome-based authentication server via the communication interface; and initiating an action associated with the transaction according to the authentication token.

A third additional embodiment of the invention includes a genome-based authentication server system. The genome-based authentication server system comprises an image database, a genome database and a genome-based authentication server. The image database is configured to store image-based token objects linked to corresponding genome-based token objects. The genome database is configured to store the genome-based token objects linked to corresponding image-based token objects. The genome-based authentication server includes at least one processor, at least one memory, at least one communication interface, and an authentication module communicatively coupled with the image database and the genome data. The at least one memory may be configured to store instructions, the instructions including instructions for the authentication module. When executed by the at least one processor, the instructions for the authentication module cause the machine to perform receiving, from an external device and via the at least one communication interface, an authentication query comprising at least one of a digital image-based token and a digital genome-based token; establishing a token pairing associated with the at least one of digital image-based token and the digital genome-based token based on corresponding linked image-based token objects and genome-based token objects in the image database and the genome database; instantiating an authentication token as a function of the token pairing; and transmitting the authentication token to the external device over the communication interface.

A fourth additional embodiment of the invention includes a transaction device. The transaction device comprises a communication interface; at least one memory, and a transaction processor coupled with the communication interface and the at least one memory. The at least one memory includes a non-transitory computer readable memory storing a genomic data structure having digital genomic data representative of an entity's genome, The at least one memory may include one or more instructions, the one or more instructions including instructions which when executed by the transaction processor, cause the transaction processor to perform identifying a partition of the genomic data structure based on a transaction request, deriving a digital transaction token from the digital genomic data with the partition, and authorizing an electronic transaction corresponding to the transaction request. Authorizing the electronic transaction also includes transmitting a digital transaction token to an external device via the communication interface.

A fifth additional embodiment of the invention includes a transaction system comprising a transaction device and a transaction server. The transaction device comprises a memory storing at least one genome-based transaction token; a communication interface coupled with the memory, and a transaction module coupled with the communication interface and configured to exchange digital data with an external device via the communication interface based, at least in part, on the at least one genome-based transaction token. The transaction server is configured to communicatively couple with the transaction device. The transaction server comprises a memory storing digital data; a communication interface coupled with the memory; and a transaction module coupled with the communication interface and configured to exchange digital data with an external device via the communication interface based, at least in part, on at least one genome-based transaction token. In an alternate embodiment, the transaction server is configured to communicatively couple with the transaction device via at least one intermediary transaction device, which comprises at least one of the following: a card reader, a cash register, a kiosk, a docking station, a smart phone, a tablet, an appliance, a television, a computer, and a vending machine.

A sixth additional embodiment of the invention includes a transaction device comprising at least one memory comprising a secure container storing transaction data; a processor coupled with the memory; a communication interface coupled with the processor; and a transaction agent. The transaction agent is configured according to software instructions stored in the at least one memory, the software instructions when executed by the processor cause the processor to receive transaction commands via the communication interface and related to an external electronic transaction; instantiate a transaction object in the memory from the transaction data based on execution of the transaction commands; generate a transaction response from the transaction object; and transmit the transaction response to an external device via the communication interface.

A seventh additional embodiment of the invention includes a transaction terminal device comprising a de minimis memory; a processor coupled with the de minimis memory; a transaction device interface coupled with the processor and configured to couple with an external transaction device; a transaction server interface coupled with the processor and configured to couple with an external transaction server over a network; and a transaction broker module. The transaction broker module is configured according to software instructions stored in the de minimis memory, the software instructions when executed on the processor cause the processor to receive a transaction request related to a transaction via at least one of the transaction device interface and the transaction server interface; generate at least one transaction command based on the transaction request; transmit the at least one transaction command to the transaction device via the transaction interface; receive a transaction response from the transaction device via the transaction device interface; and transmit the transaction response to the transaction server via the transaction server interface.

An eighth additional embodiment of the invention includes a transaction server system comprising a services database storing financial service objects that include healthcare attributes, a transaction interface, and a transaction analysis engine coupled with the services database. The transaction analysis engine comprises instructions stored in a non-transitory machine-readable medium, the instructions including instructions which when executed by a machine cause the machine to perform receiving transaction data via the transaction interface, deriving transaction healthcare attributes from the transaction data; generating a query targeting the services database from the transaction healthcare attributes; identifying at least one of the financial service objects having healthcare attributes satisfying the query; and configuring a device to present the at least one financial service object.

While the invention has been particularly described with respect to the illustrated embodiments, it will be appreciated that various alterations, modification and adaptations may be made based on the present disclosure and are intended to be within the scope of the invention. While the invention has been described in connection with what are presently considered to be the most practical and preferred embodiments, it is to be understood that the invention is not limited to the disclosed embodiments but only by the following claims.

---

What is claimed is:

1. A transaction device system associated with a user, the system comprising:
   at least one sensor configured to scan an environment including biological material of the user to derive biometric data of the user;
   at least one non-transitory computer readable memory storing one or more software instructions; and
   at least one processor coupled with the at least one sensor and the at least one memory, wherein the at least one processor performs at least the following operations upon execution of the one or more software instructions:
      storing in the at least one memory, sensor data comprising at least digital biometric data related to the user and obtained from the at least one sensor;
      generating in the at least one memory, context data from at least the digital biometric data related to the user, wherein the context data is derived at least in part from the sensor data;
      synchronizing the context data with a valid token object comprising digital data associated with the user and accessed from an authentication server;
      generating a secure session between the transaction device system and at least one computing device wherein the synchronized valid token object includes a confidence score indicating a level of match between the context data and the valid token object sufficient to authenticate the secure session;
      deriving transaction data during the secure session, including a recommendation associated with the transaction data, wherein the recommendation is derived at least in part from the context data; and
      presenting during the secure session, the recommendation associated with the transaction data to the user via a transaction interface coupled with the computing device.

2. The system of claim 1, wherein the at least one sensor comprises a camera.

3. The system of claim 2, wherein the sensor data comprises bar code image data from the camera.

4. The system of claim 1, wherein the at least one sensor comprises one or more of a global positioning system (GPS) sensor or a location sensor.

5. The system of claim 1, wherein the at least one sensor comprises a biometric sensor.

6. The system of claim 5, wherein the biometric sensor comprises a pulse ox (oximetry) sensor.

7. The system of claim 1, further comprising a personal area network coupled with the at least one processor.

8. The system of claim 7, wherein the personal area network comprises at least one wearable device.

9. The system of claim 8, wherein the wearable device comprises a smart watch.

10. The system of claim 8, wherein the wearable device comprises a smart ring.

11. The system of claim 1, wherein the digital data further include genomic data associated with the user.

12. The system of claim 11, wherein the genomic data comprises, at least in part, gene data.

13. The system of claim 12, wherein the gene data comprises gene mutation data.

14. The system of claim 12, wherein the gene data includes at least one of the following: a gene name, a gene coordinate, a short tandem repeat, a single nucleotide polymorphism, a gene variation, a codon bias, an exon- intron boundary, an exon, an intron, telomere information, a regulatory sequence, RNA coding gene, centromere information, and a gene arrangement.

15. The system of claim 1, wherein the at least one processor performs operations that further include initiating a transaction based on the recommendation via the transaction interface.

16. The system of claim 15, wherein the transaction comprises a purchase.

17. The system of claim 15, wherein the transaction comprises a healthcare transaction.

18. The system of claim 15, wherein the transaction comprises a blockchain transaction.

19. The system of claim 1, wherein the computing device comprises an external device.

20. The system of claim 19, wherein the external device comprises one of the following devices: a smart phone, a smart watch, a laptop computer, a desktop computer, a terminal, a tablet, a game console, and a point of transaction device.

* * * * *